(12) United States Patent
He et al.

(10) Patent No.: US 9,488,586 B2
(45) Date of Patent: Nov. 8, 2016

(54) DETERMINING TREATMENT FLUID COMPOSITION USING A MINI-RESERVOIR DEVICE

(71) Applicant: Multi-Chem Group, LLC, San Angelo, TX (US)

(72) Inventors: Kai He, Kingwood, TX (US); Liang Xu, The Woodlands, TX (US)

(73) Assignee: Multi-Chem Group, LLC, San Angelo, TX (US)

(*) Notice: Subject to any disclaimer, the term of this patent is extended or adjusted under 35 U.S.C. 154(b) by 0 days.

(21) Appl. No.: 14/895,464

(22) PCT Filed: Apr. 4, 2014

(86) PCT No.: PCT/US2014/032993
§ 371 (c)(1),
(2) Date: Dec. 2, 2015

(87) PCT Pub. No.: WO2015/152942
PCT Pub. Date: Oct. 8, 2015

(65) Prior Publication Data
US 2016/0123890 A1 May 5, 2016

(51) Int. Cl.
*G01N 21/84* (2006.01)
*E21B 43/00* (2006.01)
(Continued)

(52) U.S. Cl.
CPC ............ *G01N 21/84* (2013.01); *E21B 43/00* (2013.01); *E21B 47/00* (2013.01); *G01N 1/10* (2013.01); *G01N 21/05* (2013.01); *G01N 21/272* (2013.01)

(58) Field of Classification Search
CPC ...... G01N 1/10; G01N 21/05; G01N 21/272; G01N 21/84; E21B 43/00; E21B 47/00
See application file for complete search history.

(56) References Cited

U.S. PATENT DOCUMENTS 3,995,693 A 12/1976 Cornelius
4,249,608 A * 2/1981 Carter .................. C09K 8/905
166/246

(Continued)

FOREIGN PATENT DOCUMENTS

WO 9425732 A1 11/1994
WO 2009134669 A2 11/2009

OTHER PUBLICATIONS

Wu, M.J. et al. Single-and two-phase flow in microfluidic porous media analogs based on Voronoi tessellation. 2012. 9 pages.
(Continued)

*Primary Examiner* — Hezron E Williams
*Assistant Examiner* — David Z Huang
(74) *Attorney, Agent, or Firm* — Tenley R. Krueger; Baker Botts L.L.P.

(57) ABSTRACT

A mini-reservoir device may be used to screen or otherwise determine a composition of one or more treatment fluids, additives, and other fluids. Such fluids may be for use in a subterranean formation. Methods of determining a composition may include visual analysis of each of two or more fluids, each from a plurality of candidate fluids, flowed through a mini-reservoir device, and selection of one of the plurality of candidate fluids based at least in part upon that visual analysis. Certain methods may include determining an oil recovery factor for each of one or more fluids flowed through a mini-reservoir device. In particular methods, multiple treatment fluids and/or additives, such as surfactants, may be selected based at least in part upon visual analysis of the fluids' flow through a mini-reservoir device.

19 Claims, 11 Drawing Sheets

(51) Int. Cl.
*E21B 47/00* (2012.01)
*G01N 21/05* (2006.01)
*G01N 21/27* (2006.01)
*G01N 1/10* (2006.01)

(56) References Cited

U.S. PATENT DOCUMENTS 4,536,301 A * 8/1985 Malloy .............. B01F 17/0085
166/275
5,498,960 A * 3/1996 Vinegar .................... G01V 3/32
324/303
5,711,373 A * 1/1998 Lange ...................... C09K 8/58
166/252.2
2010/0006283 A1 * 1/2010 Collins .................... C09K 8/58
166/261
2010/0242586 A1 9/2010 Elshahawi et al.
2013/0071934 A1 3/2013 Indo et al.

OTHER PUBLICATIONS

Naga, S.K.G., et al. Reservoir-on-a-Chip (ROC): A new paradigm in reservoir engineering. 2011. 8 pages.
He, K. et al. Diffusive Dynamics of Nanoparticles in Arrays of Nanoposts. 2013.
He, K. et al. Validating Surfactant Performance in the Eagle Ford Shale: A Correlation between the Reservoir-on-a Chip Approach and Enhanced Well Productivity. 2014.
International Search Report and Written Opinion in related application PCT/US2014/032993, mailed on Dec. 31, 2014. 14 pages.

* cited by examiner

DETERMINING TREATMENT FLUID COMPOSITION USING A MINI-RESERVOIR DEVICE

CROSS-REFERENCE TO RELATED APPLICATION

The present application is a U.S. National Stage Application of International Application No. PCT/US2014/032993 filed Apr. 4, 2014, which is incorporated herein by reference in its entirety for all purposes.

BACKGROUND

The present disclosure relates generally to fluids and methods for their use in subterranean treatment operations (e.g., hydrocarbon recovery operations).

Treatment fluids may be used in a variety of subterranean treatments. As used herein, the term "treatment," or "treating," refers to any subterranean operation that uses a fluid in conjunction with a desired function and/or for a desired purpose. The terms "treatment," and "treating," as used herein, do not necessarily imply any particular action by the fluid or any particular component thereof. One type of treatment used in the art to increase the conductivity of a subterranean formation is hydraulic fracturing. Hydraulic fracturing operations generally involve pumping a treatment fluid (e.g., a fracturing fluid or a "pad fluid") into a well bore that penetrates a subterranean formation at or above a sufficient hydraulic pressure to create or enhance one or more pathways, or "fractures," in the subterranean formation. These fractures generally increase the permeability and/or conductivity of that portion of the formation. Other types of treatment include water flooding, acidizing, scale inhibition, corrosion inhibition, friction reduction, $CO_2$ flooding, hydrate inhibition, paraffin inhibition, and foaming, among others. Such treatments may, among other things, be used to enable or enhance recovery of hydrocarbons or other target materials from the subterranean formation (e.g., in oil and/or gas wells).

In certain circumstances, the composition of a treatment fluid may be tailored based on variations in the properties of the subterranean formation where it is used (e.g., petrophysical properties such as the pore size, wettability, porosity and permeability of rock in the formation, temperature of the formation, and/or the composition of the rock and/or embedded fluids within the formation, including oil type (if oil is present), alkalinity and/or acidity of compounds in the formation, and the like. Obtaining data relating to these properties may lead to significant delays (e.g., hours or even days) in drilling operations before efficient treatment fluids may be chosen and used. In other instances, treatment fluids may be used without regard to some or all of the formation's properties, running the risk of sub-optimal recovery of hydrocarbon or other target material from a subterranean formation.

Figure 1:
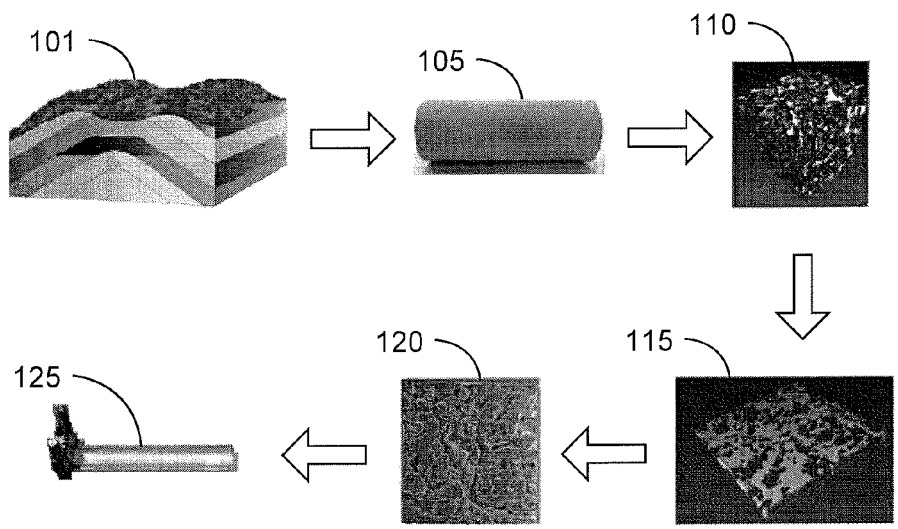
FIG. 1 is a diagram illustrating one example of a process for fabrication of a reservoir-on-chip device.

While embodiments of this disclosure have been depicted and described and are defined by reference to exemplary embodiments, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and are not exhaustive of the scope of the disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation, on-shore or off-shore. Embodiments may be applicable to injection wells, monitoring wells, and production wells, including hydrocarbon or geothermal wells.

The terms "couple" or "couples" as used herein are intended to mean either an indirect or a direct connection or incorporation. Thus, if a first device couples to a second device, that connection or incorporation may be through a direct connection, or through an indirect mechanical, acoustical, or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. It may also include one or more interface units capable of transmitting one or more signals to a controller, actuator, or like device.

As would be appreciated by those of ordinary skill in the art, with the benefit of this disclosure, one or more information handling systems may be used to implement the methods disclosed herein. Specifically, the one or more information handling systems may include machine-readable instructions to perform the methods disclosed herein. In certain embodiments, the different information handling systems may be communicatively coupled through a wired or wireless system to facilitate data transmission between the different subsystems. The structure and operation of such wired or wireless communication systems is well known to those of ordinary skill in the art having the benefit of the present disclosure and will therefore, not be discussed in detail herein. Moreover, each information handling system may include storage media and/or memory and may be any computer-readable media that stores data either permanently or temporarily.

For the purposes of this disclosure, storage media and/or memory may include any one or a combination of volatile or nonvolatile local or remote devices suitable for storing information. For example, storage media and/or memory may include a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), a solid state drive ("SSD"), flash memory, magnetic storage devices, optical storage devices, network storage devices, cloud storage devices, or any other suitable information storage device or a combination of these devices.

The present disclosure relates generally to fluids and methods for their use in subterranean treatment operations (e.g., hydrocarbon recovery operations). More particularly, the present disclosure relates to methods and systems for determining the composition of a treatment fluid. A treatment fluid whose composition is so determined may, in some embodiments, be used in a porous network, such as a porous network of a subterranean formation.

More specifically, the present disclosure provides methods for determining the composition of a treatment fluid based at least in part upon analysis in connection with flowing two or more fluid compositions through a mini-reservoir device, which device may optionally include one or more injected compounds (such as, for example, liquid and/or gaseous hydrocarbon, which may be pre-injected, injected as a previous step of the analysis, and/or co-injected with injection of a treatment fluid (on a continuous flow basis, or in concurrent or successive batch injections)). Such analysis may, in some embodiments, include visual analysis of the flow of each of the two or more fluid compositions. Suitable examples of visual analysis according to some embodiments are discussed in greater detail below. In other embodiments, analysis may also or instead include analysis of each of a plurality of effluents, each effluent comprising one of the fluid compositions and optionally any embedded compound exiting the mini-reservoir device. Effluent analysis may include, e.g., characterization of one or more properties of the effluent (such as composition, density, viscosity, polarity, degree of emulsification, and/or any other property of the effluent). Effluent analysis may be carried out by any means known in the art for analyzing effluents.

Among the many benefits and advantages of the methods and systems of the present disclosure, in certain embodiments, the treatment fluid may be selected so as to enable or enhance oil, gas, and/or other hydrocarbon recovery from the subterranean formation. Hydrocarbon recovery may be "enhanced" by a particular treatment fluid if a greater quantity of hydrocarbon is recovered over a given time period than would be recovered over the same given time period absent the treatment fluid. Increased recovery could arise from many effects, examples of which include, but are not limited to: removal of obstacles to flow such as scale or corrosion; enhancing the mobility of hydrocarbons within a formation and/or a wellbore; increasing permeability and/or conductivity of the subterranean formation to hydrocarbons and/or other fluids (e.g., by creating or enhancing one or more fractures within the subterranean formation by a fracturing operation, and/or by etching a portion of the formation, such as by acidization); and others.

For example, inclusion of a surfactant additive in a treatment fluid—and/or even the inclusion of a particular kind of surfactant as opposed to another kind—may lead to enhanced hydrocarbon recovery as compared to use of that treatment fluid without a surfactant, or without the same kind of surfactant. As a particular example, inclusion of a weakly emulsifying surfactant additive in a fracturing fluid may provide enhanced hydrocarbon recovery from a tight shale formation, as compared to the use of a non-emulsifying surfactant additive in a fracturing fluid. Likewise, in another example, use of a scale inhibitor of a particular composition may provide enhanced hydrocarbon recovery (e.g., by more effectively inhibiting scale formation in a particular formation) as compared to use of a different scale inhibitor in the same formation (even though the results might be reversed in a different formation). Accordingly, the methods of some embodiments may enable determination of a composition of a treatment fluid that provides such enhanced hydrocarbon recovery.

As noted, in certain embodiments, the treatment fluid may be for use in a porous network, such as a porous network of a subterranean formation. Such treatment fluids may have applications in, e.g., oil, gas, and/or other hydrocarbon recovery operations (such as providing, directly or indirectly, enhanced hydrocarbon recovery). In particular, certain embodiments may involve determining a treatment fluid for use in a subterranean formation. In particular embodiments, the treatment fluid may be selected from among a plurality of candidate treatment fluids based at least in part upon one of: visual analysis, effluent analysis, and combinations thereof. Methods according to certain embodiments may include determining a component to be included in a treatment fluid. In some embodiments, the component may be selected from among a plurality of candidate components. Components may according to some embodiments be any one or more of: additives; base fluids; solvents; and combinations thereof. More generally, other embodiments need not necessarily involve a plurality of candidate treatment fluids and/or candidate components. Instead, they may include: analysis of one or more fluid compositions each caused to flow through a mini-reservoir device; and subsequent inclusion of a compound in a treatment fluid and/or modification of the composition of a treatment fluid based at least in part upon the analysis of the one or more fluid compositions. The compound need not necessarily be, or need not necessarily be included in, any one or more of the analyzed fluid composition(s). For instance, the compound may be, e.g., a surfactant, corrosion inhibitor, and/or another additive or compound identified based upon the analysis of other fluid compositions.

It will be understood by one of ordinary skill in the art with the benefit of this disclosure that these are only examples of methods of determining a composition of a treatment fluid based at least in part upon analysis of treatment fluid flow through a mini-reservoir device. Other methods may be practiced which also fall within the scope of this disclosure and the claims set forth herein.

Mini-Reservoir Devices

As discussed above, methods according to some embodiments may employ a "mini-reservoir device." A mini-reservoir device according to some embodiments may be a synthetic thin slab or chip that includes a pore network. The chip may be composed of any suitable material. In some embodiments, it may comprise silicon or a silica-based substrate such as quartz; in other embodiments, it may comprise a polymer-based substrate such as polydimethylsiloxane (PDMS) and/or a thermoplastic elastomer (TPE). In particular embodiments, the surfaces of the pore network within the mini-reservoir device may be tailored to have particular surface chemistry. For example, it may be possible to tune the wettability of a mini-reservoir device's surface. For instance, a surface may have wettability that prefers oil to air, or it may preferentially water-wet. For example, a silicon chemical treatment (such as silicon vapor deposition, plasma-enhanced chemical vapor deposition (PECVD), or the like) may result in greater water wetting, while a silane chemical deposition may result in oil-wetting properties on the surface. In some embodiments, the material of construction may result in a particular wettability. For instance, PDMS-based devices may have preferential oil-wetting properties, while silicon-based devices may preferentially water-wet. In addition or instead, surface charge may be tuned by various deposition methods, such as PECVD of silicon dioxide to a surface may result in negative surface charge, while functionalization of a different compound (such as a silane, for instance 3-aminopropyltrimethoxysilane (3-APTMS)) by vapor deposition may result in positive surface charge.

The pore network (comprising pores and throats connecting the pores) may be etched or otherwise imprinted into the chip based upon one of two methodologies: (1) the pore network may be an approximation of a pore network scanned from an actual core sample, in which case the mini-reservoir device may be referred to as a "reservoir-on-chip" ("ROC") device; or (2) the pore network may be an imprint of a computationally or otherwise synthetically designed pore network, in which case the mini-reservoir device may be referred to as a "Porous Media Analog" ("PMA") device. A mini-reservoir device of either type (ROC or PMA) may in some embodiments be configured to approximate a pore network within a subterranean formation (whether by reproduction, or by generation of a structure having characteristics such as permeability and/or porosity similar to a subterranean formation, or by other means of approximation). Each type of device is discussed in greater detail below.

A reservoir-on-chip as employed in the methods of some embodiments may be formed by any suitable means for transferring an approximation of a core sample's pore structure onto a chip. In some embodiments, the approximation may constitute a three-dimensional pore network of the core sample collapsed into a two-dimensional pore network. For example, a ROC may be designed and constructed according to the flow chart shown in FIG. 1. A core plug 105 may be extracted from the formation 101. Various methods of image processing may be carried out on the core plug 105 so as to extract and visually re-construct a three-dimensional model of the plug's pore network 110. For example, the core may be sliced at a first point, and its cross section at that first point scanned (e.g., by focused ion beam-scanning electron microscopy ("FIB-SEM")); a second, thin (e.g., on nanometer or micrometer scale), slice may be removed from the core, and a second cross-section at this point scanned; and so on iteratively to create a series of cross-sectional scans of the core plug's pore network, which cross-sectional scans may be pieced back together (e.g., stacked) to model the three-dimensional pore network of the core sample. In another example, the core may be scanned by micro-computed tomography to obtain a model of the internal pore network structure. The three-dimensional pore network model 110 is then flattened to a corresponding two-dimensional pore network model 115 using a suitable method such as Delauney triangulation, or any method as described in Gunda et al., *Reservoir-on-a-Chip (ROC): A new paradigm* in reservoir engineering, LAB ON A CHIP, 2011, 11, at 3785-3792 (hereinafter "Gunda et al."), and in references cited therein. The porosity, permeability, pore size, and wettability (among other features) of the two-dimensional pore network model 115 formed according to such methods may closely approximate those of the three-dimensional pore network model 110. The two-dimensional pore network model 115 may then be used to construct a mask (e.g., a glass mask) for use in etching a replica of the two-dimensional pore network 115 onto a substrate (e.g., silicon, PDMS, or other substrate for the chip), thereby forming an etched pore network 120 on the chip 125. Inlet and outlet channels for flowing fluid through the etched pore network 120 may be in fluidic communication with the pore network. Such channels may be etched or otherwise added to the chip 125, and/or they may be coupled to inlet and outlet points on the chip. Finally, glass or another transparent substrate may be grafted to the chip so as to enable visual observation of the etched pore network 120 on the chip 125, forming the final ROC 125. An ROC alternatively may be formed by various other methods and/or variations of the above-described methods, for example as described in Gupta et al. and/or citations therein.

Figure 2:
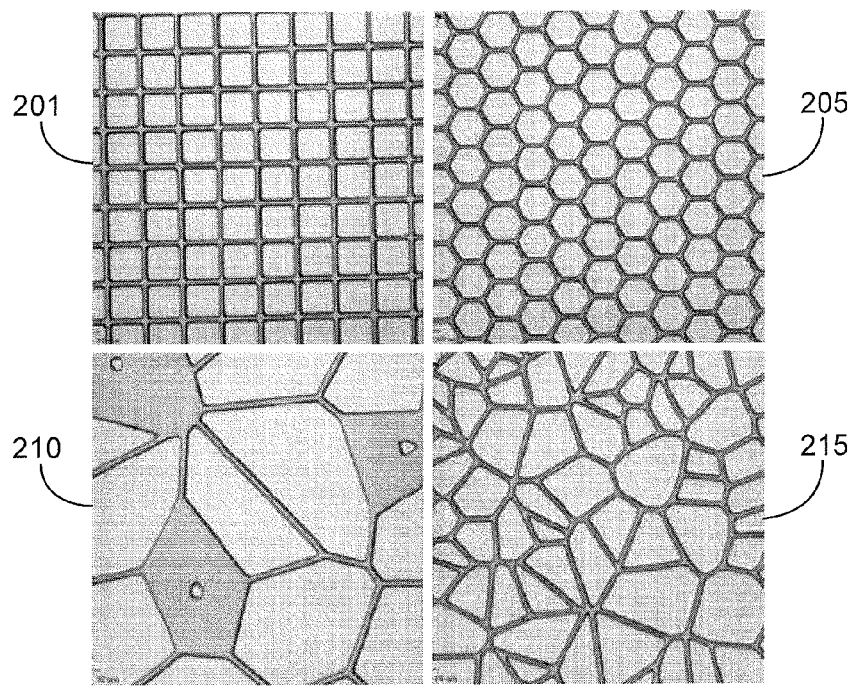
FIG. 2 is a set of illustrations each showing pore networks of sample Porous Media Analog devices.

A PMA device may be constructed by a similar methodology, with the exception that the two-dimensional pore network model is synthetically generated rather than derived from scans or other imaging of an actual core sample. Synthetic generation may be by any suitable means, such as computerized generation of a pore network of input parameters such as porosity, permeability, pore size, and wettability. In some embodiments, such generation may approximate a subterranean formation. FIG. 2 is an image captured by microscope at 100× objective showing four examples of computer-generated pore networks rendered onto mini-reservoir devices. Such networks may be of a fixed structure, such as the lattices shown in examples 201 and 205, or they may be randomized as shown in examples 210 and 215. PMA (or ROC) devices may be formed in whole or in part by methods as described by Gupta et al., and/or as described in Mao and Han, *Fabrication and characterization of 20 nm planar nanofluidic channels by glass-glass and glass-silicon bonding*, LAB ON A CHIP, 2011, 5 (8) at 837-844 (hereinafter "Mao and Han 2011"); and/or as described in Wu et al., *Single-and Two-phase Flow in Microfluidics Porous Media Analogs based on Voronoi Tessellation*, LAB ON A CHIP, 12 (2) at 253-261 (hereinafter "Wu et al. 2012").

Either type of mini-reservoir device (ROC or PMA) may in some embodiments comprise a porous network comprising micro-pores, nano-pores, or both. Micro-pores are pore, channel, and/or throat structures with generally micrometer-scale diameters (e.g., about 1 µm to about 1,000 µm); nano-pores are pore, channel, and/or throat structures with generally nanometer-scale diameters (e.g., about 1 nm to about 1,000 nm, or about 1 nm to about 400 nm, or about 1 nm to about 300 nm, or about 1 nm to about 250 nm). A mini-reservoir device (whether ROC or PMA) including pores as small as micro-pores may be referred to as a "micro-fluidic device," and a mini-reservoir device including pores as small as nano-pores may be referred to as a "nano-fluidic device." Particular embodiments may employ a nano-fluidic device, for example to determine the composition of a treatment fluid for use in a formation with low permeability and/or porosity, such as an unconventional formation (e.g., a tight shale formation).

A mini-reservoir device according to certain embodiments may include a plurality of pore networks. In such embodiments, each network may be separate (that is, one pore network may not be in fluid communication with any other pore network on the device). In certain of these embodiments, each pore network may be substantially identical. Such devices may enable parallel testing of each of multiple different fluids or fluid sets in substantially similar pore networks. In yet other embodiments, any two or more of the pore networks in a single mini-reservoir device may be different from each other.

Testing using a mini-reservoir device may include injecting one or more fluids (e.g., gases and/or liquids) into the pore network of the mini-reservoir device. As noted previously, a mini-reservoir device is structured such that it may enable visual analysis of, e.g., flow of an injected fluid through the pore network of the mini-reservoir device. Visual analysis, as used herein, includes any means of analyzing fluid flow through at least a portion of the pore network of a mini-reservoir device (and/or another characteristic related to the presence of a fluid in the mini-reservoir device), which means of analyzing is based at least in part upon: direct viewing; viewing or analysis of one or more images, and/or image data, and/or video; and combinations thereof. Visual analysis may include obtaining visual data, such as, for example: direct visual observation (e.g., the viewing and/or automated processing of one or more images, and/or the viewing of the mini-reservoir device in real time), recording of visual image data, and the like. Visual analysis may in whole or in part be automated (that is, performed in whole or in part by an information handling system executing machine-readable instructions). For example, obtaining visual data of fluid flow through the mini-reservoir device's pore network may be enabled by an imaging device like a microscope, particularly where micro- and/or nano-pore networks are being observed. In particular, an imaging device such as a microscope may be positioned proximate to a mini-reservoir device so as to enable visual observation of fluid flow within the device's pore network. Visual observation may be, e.g., through direct viewing via the imaging device. It may also or instead in whole or in part be automated. For example, the imaging device optionally may further include and/or be coupled to an image-capturing device such as a camera or other like device suitable for capturing visual image data of fluid flowing through the mini-reservoir device (e.g., for later viewing of an image or images, and/or later playback of video). Particular embodiments may employ, for example, a microscope equipped with a motorized stage and a high speed, high resolution camera. High speed cameras may in some embodiments enable detailed analysis of fluid flow.

In addition or instead, capturing visual image data may include image processing of a currently observable image, and/or of one or more captured images or video (e.g., automated image recognition). In certain embodiments, then, an imaging device and/or an image-capturing device may be electronically coupled to an information handling system. The information handling system may include memory comprising machine-readable instructions that, when executed, cause the information handling system to capture one or more images of the micro-fluidic device (and any fluid within the device). In addition or instead, the memory may comprise machine-readable instructions that, when executed, cause the information handling system to perform visual analysis of image data of the mini-reservoir device. An example of such visual analysis may include, for example, comparison of volume of any one or more fluids in the pore network of the mini-reservoir device between any two or more images (and/or between any two or more videos). For instance, image subtraction may enable automated (at least in part) determination of relative volumes of a given fluid in the pore network at two different times.

Furthermore, to aid in or otherwise accompany visual analysis, one or more dyes or other contrast agents may be added to any one or more fluids (hydrocarbon or otherwise) to be flowed through the device. Such dye or contrast agent may enhance the contrast between two or more fluids (and/or two or more phases) flowing through the device, thereby enabling clearer visual analysis. For instance, food coloring dye may be added to a fluid flowed through the mini-reservoir device at the same time as a hydrocarbon fluid, so as to better enable viewing of the dyed fluid as contrasted with the hydrocarbon fluid and/or the mini-reservoir device. In some embodiments, dying one or more fluids flowing through the device may enable visual analysis of interaction between two or more fluids, such as the formation of emulsions.

In methods according to some embodiments, mini-reservoir devices may allow for superior repeatability of testing as compared to other testing means, such as core sample testing. For instance, in some embodiments, two or more mini-reservoir devices each with identical pore structures may be fabricated, allowing tests of multiple fluid compositions to be carried out in parallel. In some embodiments, a mini-reservoir device may be discarded after use (due to, e.g., entrained fluid composition, device pore damage during testing, or the like) in order to ensure maximum accuracy of analytical data. Thus, fabrication of multiple mini-reservoir devices need not necessarily require parallel testing of fluid compositions; instead, in the methods of some embodiments, multiple mini-reservoir devices may simply be needed for two or more successive procedures. In other embodiments, however, a mini-reservoir device may be reused, optionally with cleaning (e.g., by nitrogen gas injection or other suitable method) between each use.

Methods of Testing Using a Mini-Reservoir Device

Figure 3:
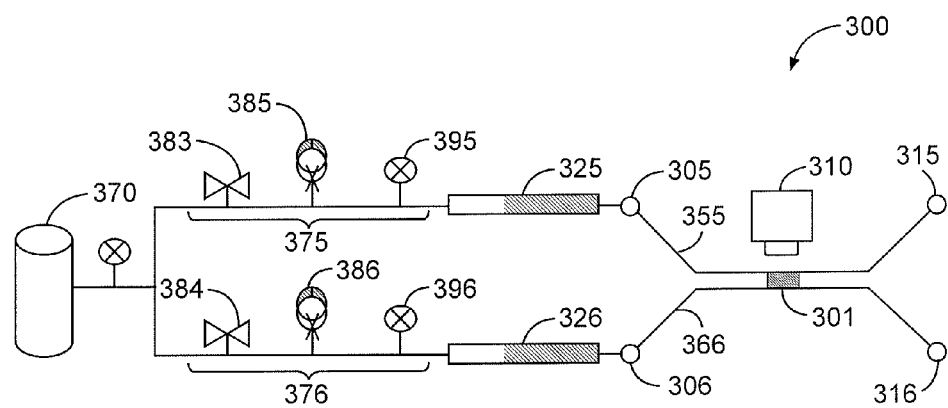
FIG. 3 is a schematic diagram of a system set-up to perform methods in accordance with some embodiments of the present disclosure.

A method according to some example embodiments may be described in part by reference to FIG. 3. FIG. 3 is a diagram illustrating an example system 300 of equipment for use in methods of determining the composition of a treatment fluid according to some embodiments. The mini-reservoir device 301 includes a pore network that is in fluid communication with each of two inlets (305 and 306) and two outlets (315 and 316). The tubing of each inlet-outlet pair (305 plus 315, and 306 plus 316) forms a first and second channel 355 and 366, respectively. An imaging device 310 is positioned proximate to the mini-reservoir device 301. Although not shown in FIG. 3, the imaging device 310 may in some embodiments be communicatively coupled to an information handling system, as previously discussed. The imaging device may aid in, or enable, visual analysis of fluid flow through the mini-reservoir device 301 in accordance with the previous discussion of visual analysis. First and second capillary tubes 325 and 326 are in fluid communication with each respective channel 355 and 366, and may hold either or both of a fluid for analysis (e.g., a candidate treatment fluid, candidate additive, or other fluid) and liquid and/or gaseous hydrocarbon (e.g., natural gas, crude oil, and the like). Each capillary tube 325 and 326 may further include an inlet or other means for accepting additional fluid (not shown). A driving gas source 370 is connected to each of the capillaries 325 and 326 through first and second conduits (375 and 376, respectively), each conduit respectively including first and second pressure regulators 385 and 386 for independently regulating flow of the driving gas into each capillary 325 and 326 (and pressure switches 383 and 384 for shutting off or enabling flow), so as to drive each fluid in each capillary into the channels 355 and 366 at controllable pressures. First and second pressure gauges 395 and 396 may enable monitoring of the driving pressure.

The first capillary tube 325 may be loaded with liquid hydrocarbon, and the second capillary tube 326 may be loaded with a candidate additive, such as a surfactant. The liquid hydrocarbon may in some embodiments be crude oil, natural gas, other liquid hydrocarbon, and combinations thereof. It may be sourced from a particular subterranean formation of interest (e.g., a subterranean formation in which one of a plurality of candidate additives are being studied for use). The first pressure regulator 385 may be set to enable flow of compressed gas (e.g., compressed nitrogen gas) from gas source 370 through the first conduit 375 and into the first capillary 325, pushing the liquid hydrocarbon via the first inlet 305 into the first channel 355, into the mini-reservoir device 301, and in turn through the first outlet 315. As noted, the surfaces of the pore network within the mini-reservoir device may in some embodiments be fabricated such that they have wettability that prefers oil to air. Thus, the liquid hydrocarbon may infiltrate the pore network via the first channel 355, rather than only passing through the channel 355 and out via the first outlet 315. In methods according to some embodiments, the liquid hydrocarbon may be allowed to reach a continuous and/or steady-state flow, whereupon the second pressure regulator 386 allows flow of gas into the second conduit 376 so as to push the candidate additive from the second capillary 326 into the mini-reservoir device 301 via the second inlet 306, through the second channel 366, and out of the device via the second outlet 316. In embodiments wherein the device 301 is preferably oil-wetting, a low initial driving pressure of the candidate fluid may result in the candidate fluid flowing through the second channel 366 and out the second outlet 316, without breaking through the pore network of the mini-reservoir device (that is, without flowing in a path through at least some of the pore network so as to reach the opposite channel, here first channel 365). In certain other embodiments, on the other hand, the mini-reservoir device may instead be preferentially wetting to an aqueous phase, and the candidate fluid may be in aqueous phase, therefore allowing the candidate fluid to more easily break through (but making it more difficult for the oil to break through when injected). One of ordinary skill in the art with the benefit of this disclosure will recognize when a particular application requires preferable oil- or water-wetting of the mini-reservoir device's pore network surfaces (based, e.g., on properties of a formation or other pore network currently being studied). Surface properties such as preferential wettability may be designed and built into a mini-reservoir device according to any suitable method, including those discussed previously herein. In addition, in some embodiments, either or both outlets 315 and 316 may be closed so as to direct flow of either fluid in a desired manner (e.g., second outlet 316 may be closed to help direct a candidate fluid from the second channel 366 through the pore network of the mini-reservoir device 301 and out the first outlet 315).

The remainder of this example method will be described in accordance with embodiments wherein the mini-reservoir device 301 is preferentially oil-wetting, and further in accordance with embodiments wherein the candidate fluid is an aqueous phase fluid. Thus, an initial drive pressure of the candidate fluid may not result in breakthrough. The methods of some embodiments may therefore include varying drive pressure of a fluid being injected into the mini-reservoir device. For instance, the drive pressure of the candidate fluid in this example embodiment may be varied upwards (e.g., until breakthrough occurs). The pressure optionally may then be varied further. For instance, it may be further increased in order to achieve desired effects and/or obtain desired observations. In particular, the drive pressure may be increased so as to achieve more complete (or substantially complete) displacement of the hydrocarbon phase embedded in the pore network of the mini-reservoir device. It may be increased so as to achieve complete or near-complete penetration by the candidate fluid of pores and/or throats within the pore network.

During any point or points of the above-discussed flow processes (of hydrocarbon and/or candidate fluid, in this example embodiment), imaging device 310 may allow observation of live images of fluid flow through the mini-reservoir device. It may also or instead capture one or more images and/or videos of flow, and may further cause any of the one or more images and/or video to be recorded (e.g., stored on machine-readable medium in a coupled information handling system (not shown in FIG. 3)). Visual analysis of such images and/or video (whether live or viewed later) may provide insight as to various parameters such as breakthrough pressure, hydrocarbon displacement, flow characteristics of any one or more fluids passing through the mini-reservoir device's pore network, and the like. In certain embodiments, as previously noted, such analysis may be in whole or in part automated. For instance, image processing software or similar means may be stored on machine-readable media of an information handling system, and may be capable, e.g., of determining volumes of hydrocarbon or other fluid entrained within the pore network of the mini-reservoir device at each of any one or more given times. Comparison between multiple images may enable, e.g., image subtraction for determining volume differences of any one or more fluids vs. time.

Furthermore, each of multiple fluids may be tracked and/or analyzed in a similar manner. For instance, returning to example embodiments using equipment such as shown in FIG. 3, each of two or more candidate fluids may be injected during different procedures within the same method. That is, a first candidate fluid may be injected (e.g., through second capillary 326 into second channel 366, and from there into the mini-reservoir device 301 and out via either or both of the first and second outlets 315 and 316), the injection of the first candidate fluid may be ceased, and a second candidate fluid thereafter may be injected similarly, optionally followed by a third candidate fluid, and so on. Other embodiments may involve the injection of each candidate fluid into each of multiple mini-reservoir devices (either in parallel procedures or in succession, or partially overlapping). Similarly, other embodiments may involve the injection of each candidate fluid into each of multiple pore networks in a single mini-reservoir device. In such embodiments involving parallel methodologies, then, the potential for cross-contamination (e.g., from left-over candidate fluid from a previous injection) may be minimized, thereby allowing for better control and more accurate analysis based solely upon the candidate fluid currently being injected.

Figure 4:
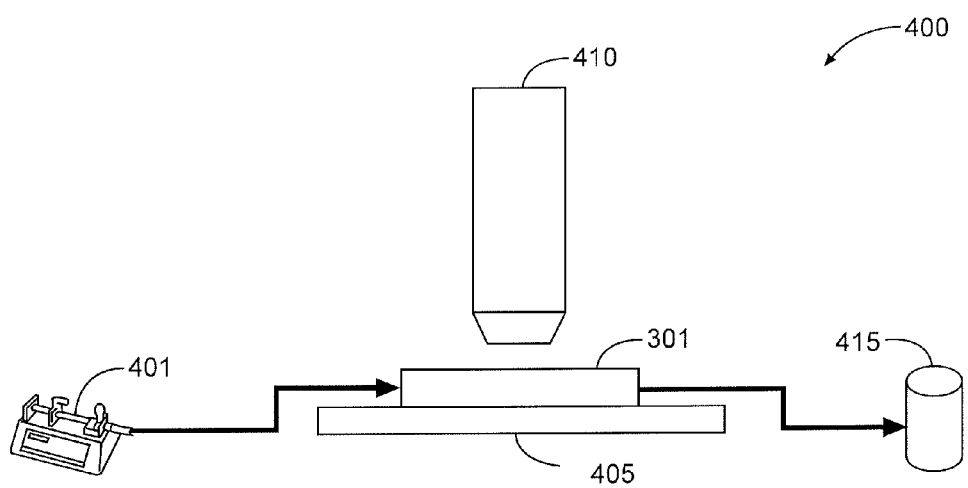
FIG. 4 is a schematic diagram of a system set-up to perform methods in accordance with some embodiments of the present disclosure.

It will further be appreciated that various set-ups may be used according to some embodiments. For instance, FIG. 4 demonstrates another example set-up including a syringe pump 401 for injection of a candidate fluid and/or fluid hydrocarbon into mini-reservoir device 301, which may be disposed on a motorized stage 405 of a microscope 410. Effluent may be collected in any suitable container 415. Any element or elements of FIGS. 3 and 4 may, of course, be combined to yield further example configurations for carrying out methods described herein (e.g., a microscope and motorized stage assembly could be used as imaging device 310; and/or a gas source with pressure switches and/or regulators may be used in place of the syringe pump 401 in the assembly 400 of FIG. 4). Further, these example assemblies 300 and 400 are used herein only to demonstrate examples of assemblies suitable for performing the methods described herein. Those of ordinary skill in the art, with the benefit of this disclosure, will readily recognize any variations or other assemblies that may be used with methods of the present disclosure.

Furthermore, as noted, drive pressures may vary over time in some embodiments. In particular, drive pressure (as measured at or before an inlet to the mini-reservoir device) during injection may vary from about 1 psig to about 5,000 psig. In particular embodiments, it may range from about 1 psig to about 100 psig, and in other embodiments from about 1 to about 50 psig. In certain other embodiments, drive pressure may vary from about 1 to about 60 psig; from about 1 to about 40 psig; from about 1 to about 20 psig. In certain embodiments, pressure may increase over time, such that injection starts at an initial drive pressure $P_1$ and thereafter is varied to a higher drive pressure $P_2$. Initial drive pressures (for hydrocarbon, candidate fluid, and/or any fluid being injected into the mini-reservoir device) according to various embodiments may range from about 1 psig to about 5,000 psig in some embodiments. In certain embodiments, initial drive pressure may be approximately any integer value between 1 and 100 psig. Thus, for example, an initial drive pressure according to such embodiments may be any one of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and so on up to 100 psig. Each of a second, third, fourth, fifth, or greater drive pressure of injection reached after the initial drive pressure may in some embodiments be higher than the initial drive pressure, and may be any integer value between 1 and 100 psig. In certain embodiments, each successive drive pressure may be higher than the previous drive pressure. Yet, in certain other embodiments, successive drive pressures may be lower, and in some embodiments any one or more successive drive pressures may be lower than the initial drive pressure.

Analysis

Analysis may follow the injection or injections (in whatever assembly), and a treatment fluid, additive, or other fluid may be selected from among the group of candidate fluids (e.g., for use in a subterranean formation of interest) based at least in part upon said analysis. Analysis may include visual analysis (as described above), and/or it may include analysis of one or more effluents from the process (e.g., analysis of at least part of the fluid or fluids expelled through the first and/or second outlets 315 and 316 during at least part of the process).

Figure 5:
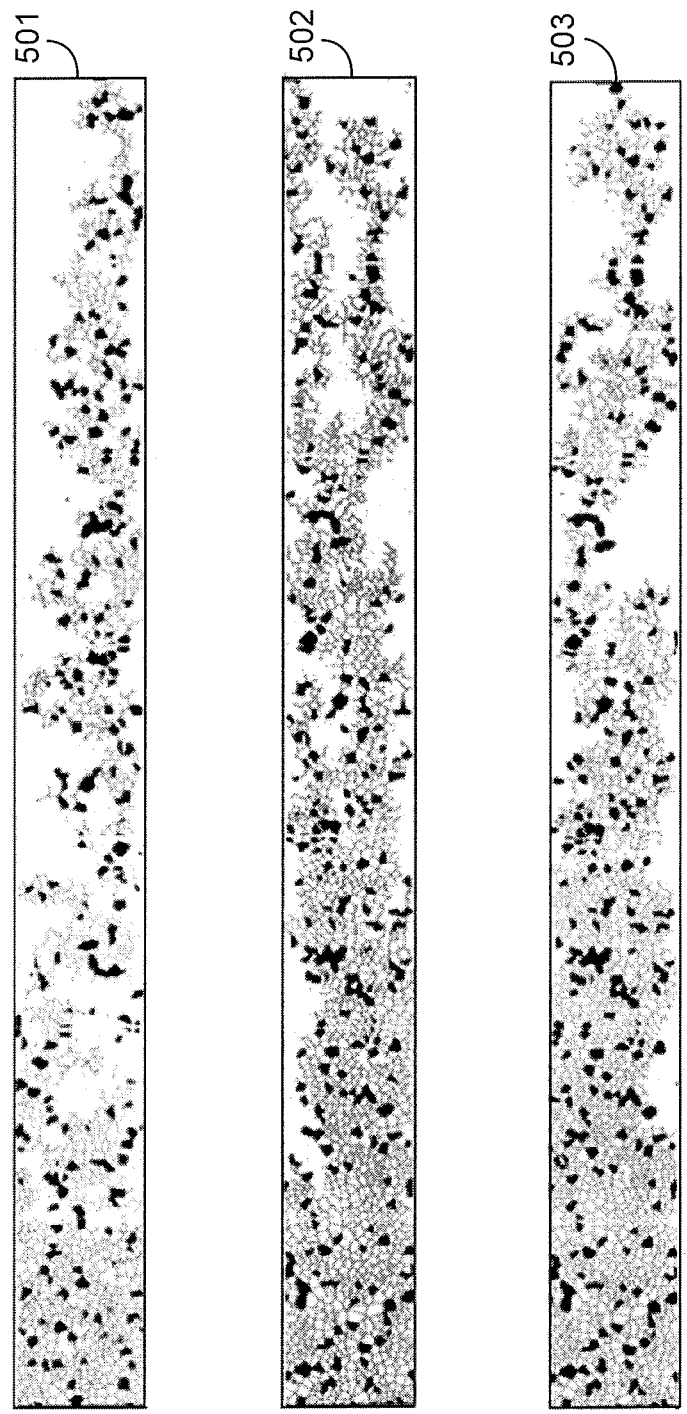
FIG. 5 is a set of images illustrating visual analysis of fluid saturation in a mini-reservoir device in accordance with some embodiments of the present disclosure.

An example of visual analysis according to some embodiments may be described by reference to FIG. 5. FIG. 5 is a set of example microscope images taken at 20× objective, each image showing a different candidate treatment fluid's distribution through each of three identical pore networks on three identical mini-reservoir devices. These images were captured by an imaging device, such as imaging device 310, during injection of each separate candidate treatment fluid into each respective mini-reservoir device. Candidate treatment fluids are shown in black. The images readily lend themselves to visual analysis, whether by direct observation or by whole or partial automation. For instance, example image 502 shows the second candidate treatment fluid's more extensive penetration into the pore network (demonstrated by the greater number of pores and channels within the network shown with black-colored treatment fluid disposed therein), as compared to either the first candidate treatment fluid (image 501) or the third candidate treatment fluid (image 503).

Figure 6:
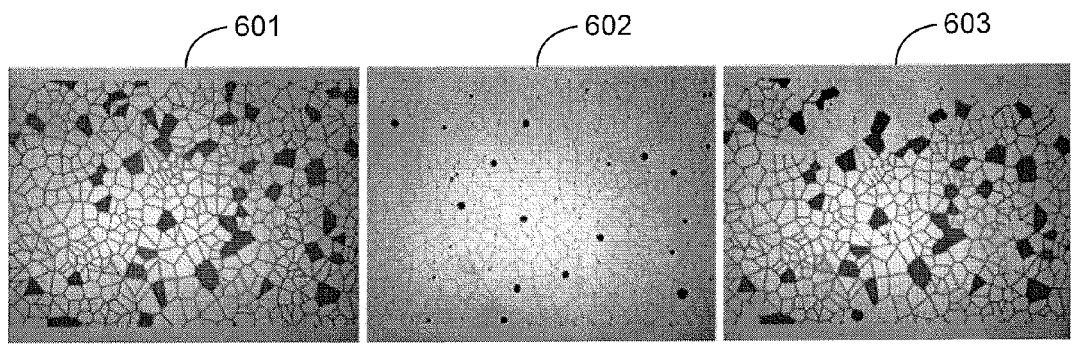
FIG. 6 is a set of images illustrating visual analysis of fluid saturation in a mini-reservoir device in accordance with some embodiments of the present disclosure.

Another example of visual analysis according to some embodiments may be described by reference to FIG. 6. FIG. 6 is a series of microscope images at 20× objective taken at different times during the same set of injections into the same mini-reservoir device. First, a preliminary fluid (such as a brine or other aqueous phase fluid) was injected into the mini-reservoir device at sufficient drive pressure such that it saturated a substantial portion of the pore network of the mini-reservoir device, and an image 601 of that saturation was captured. Partial saturation of the pore network by the brine is shown by the darkened pores and channels in image 601. Oil was then injected into the mini-reservoir device, and a second image 602 taken. The dark spots in second image 602 show some remnant entrained brine. Then, a candidate treatment fluid (in this example, a surfactant) was injected into the mini-reservoir device and a third image 603 captured. The darkened areas of the third image 603 show where surfactant saturated the pore network. As noted previously, to aid in visual analysis, a candidate fluid may in some embodiments be mixed with or may include a dye, contrast agent, or the like during injection into the mini-reservoir device. Such a dye, contrast agent, or the like may aid in identification of the fluid in any one or more images (as shown by example in images 601-603, wherein the fluid shows in darker black relative to the rest of the image).

From these images, the preliminary fluid (e.g., brine) volume shown in image 601 may be used to determine initial water saturation $S_{iw}$ of the pore network; remaining brine volume in image 602 may be used to determine irreducible water saturation $S_{wt}$; and the volume of the candidate treatment fluid shown in image 603 may be used to determine treatment fluid saturation $S_f$. In some embodiments, these values may be determined by image processing, such as by a software program stored on machine-readable media in or coupled to an information handling system which, when executed, is capable of recognizing the black (fluid-saturated) areas of each image, and/or of computing relative saturation based on those areas. For example, publically available software ImageJ (a public domain image processing program available from the National Institutes of Health) may be used, for instance (with or without user modification adapted to capturing, recording, and/or processing microscope or other images). Instead or in addition, code in the "MATLAB®" program, available from MathWorks, Inc., may be used. Once processing determines each of $S_{iw}$, $S_{wt}$, and $S_f$, an oil recovery factor (RF) may be calculated as:

$$RF = (S_f - S_{wt})/(S_{iw} - S_{wt})$$ (Eqn. 1)

In methods according to some embodiments, the initial preliminary fluid saturation step may be skipped, and instead visual analysis of an image following oil or other hydrocarbon injection (corresponding to the second image 602) may be used to determine oil or other hydrocarbon saturation $S_o$. In certain embodiments, as previously noted, a dye or contrast agent may be mixed with injected oil or other hydrocarbon to aid in visual recognition. In such embodiments, RF may still be calculated as:

$$RF = S_f/S_o$$ (Eqn. 2)

These are only examples of determining RF; other methods may be employed according to some embodiments of the present disclosure.

Figure 7:
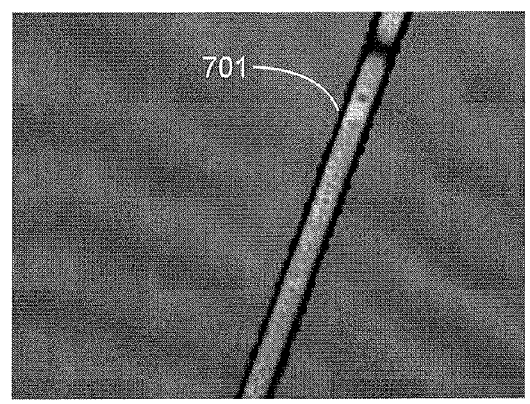
FIG. 7 is an image illustrating one example of an oil-in-water emulsion in a nanochannel.

In yet further example embodiments, analysis may also or instead include visual analysis to identify a desired property. For example, where one wishes to test candidate surfactants to determine which, if any, will emulsify oil in the porous network, one could obtain one or more images from the above processes and observe said image(s) to determine whether emulsification occurred. For instance, FIG. 7 is an optical micrograph at 50× objective from which emulsified oil droplets 701 in a nano-pore 705 may be observed, showing that the surfactant observed in FIG. 7 does indeed emulsify oil in nanoscopic pore structures. Thus, if a requirement of a candidate treatment fluid is that it be capable of emulsifying oil in nanoscopic pores, analysis of FIG. 7 may lead to determination to use the candidate fluid imaged in FIG. 7. In further examples along similar lines, visual analysis in some embodiments may include comparing emulsion tendency of each of two or more fluids. For example, the tendency of each fluid to emulsify hydrocarbon may be assessed and/or compared. Emulsion tendency evaluation may include assessment of whether a fluid is capable of forming emulsions (e.g., whether it is capable of emulsifying oil, or in other words forming an oil-in-water emulsion). It may also or instead include quantification of phase separation rates and/or emulsion droplet size and droplet size distribution. Such quantification may be based at least in part upon visual data obtained during flowing of one or more fluids through the mini-reservoir device. Methods including such emulsion tendency analysis may further include shaking or otherwise agitating the mini-reservoir device while it contains one or more fluids in it, so as to enable observation of emulsion tendency.

Further, as previously discussed, another example of analysis may include effluent analysis. Effluent analysis may include, e.g., characterization of composition and/or one or more other properties (density, viscosity, pH, etc.) of an effluent from the mini-reservoir device. Test and selection procedures may be tailored to obtain a particular effluent in some embodiments. For example, effluent may comprise a portion of a candidate fluid and a portion of hydrocarbon displaced by the candidate fluid during injection of the candidate fluid. On the other hand, in other examples, effluent may comprise the entirety of hydrocarbon and candidate fluid flowed through the mini-reservoir device. Effluent may be analyzed by any suitable chemical analytical technique such as UV, IR, NMR, chromatography, and/or any other chemical analytical technique.

Analysis (whether visual analysis, effluent analysis, or other analysis) may in some embodiments include comparing the relative characteristics of each of two or more candidate fluids. For instance, analyses and/or calculations may be carried out in accordance with the above description, and from such analyses, comparisons of, e.g., relative oil recovery factors, relative effectiveness, relative emulsification, and/or other relative characteristics as between two or more candidate fluids may be determined. In particular, for example, comparing the relative characteristics of each of two or more fluids may include determining the fluid resulting in the greatest oil recovery factor, and/or resulting in the greatest observed saturation of the pore network, and/or resulting in the least erosion of surfaces of the pore network, and/or resulting in the least formation of sediment or other particulate matter in the pore network.

Determination of Compositions

The above methodologies and analyses are some examples of methods that may be used for determining a composition for a fluid (e.g., a treatment fluid). For instance, they may be used in some embodiments to determine the composition of an additive, or to determine the identity of an additive, to be included in, a treatment fluid.

In some embodiments, such methods of determination may include selecting a treatment fluid from among a plurality of candidate treatment fluids, the selection being based at least in part upon analysis (e.g., of the flow characteristics and/or effluent characteristics of one or more of the candidate treatment fluids injected into one or more mini-reservoir devices). The selected treatment fluid may be used in, e.g., a subterranean formation (such as in a hydrocarbon recovery process in the subterranean formation). Likewise, in some embodiments, methods of determination may include selecting an additive from among a plurality of candidate additives, the selected additive being incorporated in a treatment or other fluid (e.g., for use in hydrocarbon recovery or other operations in a subterranean formation).

In other embodiments, such methods of determination may include determining a composition of a treatment fluid based at least in part upon analysis of one or more fluids injected through a mini-reservoir device.

In yet other embodiments, methods of determination may include determining not to use a treatment fluid or an additive, based at least in part upon analysis of one or more treatment fluids (or one or more additives) injected into one or more mini-reservoir devices.

Treatment Fluids

Each of the plurality of candidate fluids may include a different type and/or different composition of the candidate fluid. For example, a first candidate additive may be a weakly emulsifying surfactant, a second candidate additive may be a non-emulsifying surfactant, and a third candidate additive may be a strongly-emulsifying surfactant. Weakly emulsifying surfactants may include any surfactant capable of forming relatively short-lived, or transient, oil-in-acid, oil-in-water, or other oil-in-aqueous phase emulsions. In some embodiments, suitable weakly emulsifying surfactants may be characterized by their capability to form one or more oil-in-aqueous phase emulsions that break and reform whenever the emulsion is subjected to shear forces. Thus, in some embodiments, selection of a treatment fluid including a weakly emulsifying surfactant in a formation may result in emulsions that break apart and reform when subjected to shear flow in the formation.

In yet further embodiments, selection may be between multiple surfactants—for example, so as to select the surfactant(s) best demonstrating desired properties, such as selecting the most weakly-emulsifying surfactant from among candidate surfactants, or such as selecting the least emulsifying (i.e., most "non-emulsifying") surfactant. In some embodiments, visual analysis may help identify a weakly- or a non-emulsifying surfactant. For instance, a plurality of images taken over a given time period may be analyzed to determine whether the formation and breaking apart of oil-in-aqueous phase emulsions takes place, as may be consistent with a weakly-emulsifying surfactant. On the other hand, in other embodiments, images may be analyzed to determine the absence of emulsions so as to select a non-emulsifying surfactant. The selected surfactant may be included in a treatment fluid. For example, in some embodiments, it may be included in a fracturing fluid. Similarly, methods according to some embodiments may include selecting a fracturing fluid from among candidate fracturing fluids, each candidate fracturing fluid comprising a different surfactant.

In another example according to some embodiments, a first candidate treatment fluid may comprise a weakly-emulsifying surfactant; a second candidate treatment fluid may comprise a non-emulsifying surfactant; a third candidate treatment fluid may comprise a strongly-emulsifying surfactant; and a fourth candidate treatment fluid may comprise substantially no surfactant. Each of the four may be injected into a mini-reservoir device and analyzed in accordance with embodiments described herein. Analysis may include, e.g., computation of an oil recovery factor, and the candidate surfactant resulting in the greatest oil recovery factor may be selected for use in a subterranean formation.

In yet another example embodiment, each of two or more candidate treatment fluids and/or candidate additives may each comprise a weakly emulsifying surfactant. Each candidate fluid may be injected and analyzed so as to assess, e.g., emulsification tendency. In some instances, the same candidate fluids may exhibit different properties in different subterranean formations; thus, the same set of candidate fluids may be tested in each of multiple tests, each test including use of a different mini-reservoir device (e.g., each device may have different construction, surface chemistry, or the like, so as to reflect differences among different subterranean formations, as discussed elsewhere herein).

Other candidate fluids may be assessed and/or selected according to other embodiments. For example, candidate fluids (e.g., candidate treatment fluids and/or candidate additives) may in certain embodiments each comprise a compound selected from the group consisting of: surfactants; acids; scale inhibitors; corrosion inhibitors; friction reducers; gas injection gases; hydrate inhibitors; paraffin inhibitors; foaming agents; viscosifying agents; emulsion breakers; biocides; and combinations thereof.

Furthermore, the terms "candidate additive," "candidate treatment fluid," "candidate fluid," and the like, are not necessarily meant to imply any particular degree, or even existence, of consideration of such additives or treatment fluids for any particular purpose. Rather, they are meant only to help distinguish between a group of fluids tested, and a fluid actually selected from among the group of fluids tested, and/or from a subset of that group (in embodiments where selection from a group is applicable). Similarly, a selected fluid may in some embodiments not necessarily be from the group of those tested; instead, analysis of candidate treatment fluids and/or additive may lead to the determination to use none of those fluids and/or additives. It may likewise lead to determination to use another fluid or additive entirely. Candidate fluids or the like may alternatively be described simply as second fluids, third fluids, fourth fluids, and so on, in a manner to distinguish them from hydrocarbon fluids that may be concurrently, previously, and/or subsequently injected into a mini-reservoir device into which a candidate fluid is, has been, or will be injected.

Nonetheless, reference to a plurality of candidate fluids (and/or treatment fluids, additives, and the like) according to some embodiments may identify a group of fluids being tested or considered for introduction to a subterranean formation; and/or such reference may identify a group of fluids that may be suitable for introduction to a subterranean formation. In particular embodiments, the group of suitable fluids may be those suitable for a certain purpose (e.g., a group of suitable surfactants, emulsion breakers, paraffin inhibitors, hydrate inhibitors, viscosifying agents, friction reducers, corrosion inhibitors, scale inhibitors, acids, biocides, foaming agents, etc.).

The example methods and analyses described above include particular and specific examples of methodologies according only to some embodiments of the present disclosure. Other systems and methods are possible according to various embodiments, and some embodiments may include more general methods, which methods are not necessarily limited by particular means of injection, or particular analysis, etc.

For example, liquid hydrocarbon may be injected by any suitable means into a pore network of a mini-reservoir device, such as by suitably high driving pressure and location of an outlet such that the liquid hydrocarbon must pass through the pore network to reach the outlet. Thus, the mini-reservoir device need not necessarily be constructed to preferentially be wetted by hydrocarbon over air. In addition, the driving pressure of the liquid hydrocarbon need not necessarily be held constant; it may be varied during the method. Further, one or more outlets may be closed (where more than one outlet is present) once liquid hydrocarbon substantially wets the pore network's channels, and/or the driving force to the liquid hydrocarbon may be discontinued (e.g., a drive gas regulator may be closed), thereby resulting in embedded hydrocarbon in the pore network of the mini-reservoir device. Alternatively, the driving force of the liquid hydrocarbon may be cut off while leaving an outlet open, thereby allowing at least a portion (but not necessarily all) of the liquid hydrocarbon within the pore network to remain in the pore network. Thus, in general, injecting liquid hydrocarbon into a pore network of a mini-reservoir device may in some embodiments include either: (1) steady-state and/or continuous flow injection, or (2) batch injection. The same methodologies could equally apply in some embodiments to any other injected fluid (e.g., a candidate additive, candidate treatment fluid, or other compound injected into the mini-reservoir device), such that injecting any fluid into a pore network of a mini-reservoir device may likewise include either steady-state and/or continuous flow injection, or batch injection. Further, as described, batch injection may be coupled with closure of an outlet. One of ordinary skill in the art with the benefit of this disclosure will recognize the circumstances in which any one or more of various types of injection may be suitable.

It will further be apparent that these distinct sub-types of injection may lead to different methodologies in accordance with yet further embodiments, such as discrete injection of liquid hydrocarbon and other fluid into the pore network of a mini-reservoir device. That is, the methods of some embodiments may include: injecting liquid hydrocarbon into the pore network; ceasing injection of the liquid hydrocarbon; and after then injecting a candidate treatment fluid (and/or a candidate additive or other fluid) into the pore network. On the other hand, methods of other embodiments may, similar to the detailed description above referencing FIG. 3, include at least partially concurrent injection of liquid hydrocarbon and a candidate fluid. That is, during at least some period of time, both liquid hydrocarbon and candidate fluid may be injected substantially simultaneously into the mini-reservoir device (although it will be appreciated that such injections may or may not be of equal driving pressures and/or equal flow rates).

It will therefore be appreciated by one of ordinary skill in the art, with the benefit of this disclosure, that many different hydrocarbon recovery processes (among other processes) may be simulated according to the methods of various embodiments. For example, embodiments in accordance with the methods discussed above in connection with FIG. 3, and particularly those certain embodiments involving at least partially concurrent injection of two or more fluids, may provide examples of simulation of a co-carbon recovery process (e.g., a process such as a water flood in which treatment fluid and hydrocarbon flow in the same direction, as may occur, e.g., in a two-well set-up including a production and an injection well). Other methods according to other embodiments may simulate counter-carbon production methods, such as may be seen in hydraulic and/or acid fracturing processes (e.g., processes wherein treatment fluid flows into the subterranean formation from a wellbore, and hydrocarbon flows out of the subterranean formation into the same wellbore, generally counter-flow with respect to the direction of flow of the treatment fluid). For instance, methods involving the embedding of hydrocarbon in the mini-reservoir device followed by injection of one or more other fluids may be used to simulate counter-carbon processes such as hydraulic fracturing.

Furthermore, as has been noted, various fluids may be evaluated by methods according to the various embodiments of the present disclosure. For instance, each of a plurality of candidate treatment fluids and/or candidate additives for treatment fluids may be assessed. In particular, a candidate additive may be or include any one or more of (and/or a candidate treatment fluid may comprise any one or more of) the following: a surfactant, a corrosion inhibitor, a scale inhibitor, a gas for gas injection, a hydrate inhibitor, a paraffin inhibitor, a foaming agent, a friction reducer, a viscosifying agent, a biocide, an emulsion breaker, and combinations thereof.

To enable a greater understanding of the present disclosure, additional example methods according to various embodiments are discussed below. In general, except to the extent otherwise noted below, previous descriptions of the various specific aspects of the following methods (such as range of potential candidate fluids, types of analyses, various methodologies for injection, etc.) apply equally to the embodiments discussed below. For example, a reference in a below-discussed method to injection, injecting, or the like may include any methods of injection consistent with the above discussion of injection of liquid hydrocarbon and other fluids into a porous network of a mini-reservoir device.

A method according to some example embodiments may include: injecting a first portion of a hydrocarbon fluid into a pore network of a mini-reservoir device; injecting a second fluid into the pore network; analyzing the second fluid's flow through the pore network of the mini-reservoir device; and based at least in part upon the analysis of the second fluid's flow, determining a composition of a treatment fluid for use in a subterranean formation. In some embodiments, the method may further include injecting a second hydrocarbon fluid into a pore network of a second mini-reservoir device; injecting a fourth fluid into the pore network of the second mini-reservoir device; and analyzing the fourth fluid's flow through the pore network of the second mini-reservoir device. Determining a composition of a treatment fluid in such embodiments may further be based at least in part upon the analysis of the fourth fluid's flow. In certain embodiments, either of the second fluid or the fourth fluid may independently be selected from the group consisting of: candidate treatment fluids, candidate additives, and combinations thereof. In particular of those embodiments, determining a composition of a treatment fluid may include selecting either the second or the third fluid for use as a treatment fluid, or for inclusion in a treatment fluid. Other embodiments may similarly involve a third hydrocarbon fluid injected into a pore network of a third mini-reservoir device, and injection of a sixth fluid into the pore network of the third mini-reservoir device, and so on, with analysis encompassing each injected second, fourth, sixth, etc. fluids (and in some embodiments, including comparing relative characteristics of the second, fourth, sixth, etc. fluids).

A 1st embodiment may include a method comprising: injecting a first candidate fluid into a pore network of a first mini-reservoir device; injecting a second candidate fluid into a pore network of a second mini-reservoir device; obtaining first visual data of the flow of the first candidate fluid through the first mini-reservoir device; obtaining second visual data of the flow of the second candidate fluid through the second mini-reservoir device; and based at least in part upon visual analysis of the first and second visual data, selecting a fluid for introduction into a subterranean formation.

A 2nd embodiment may include a method according to the first embodiment, wherein the first and second candidate fluids are from among a plurality of candidate fluids; each one of the plurality of candidate fluids comprises a compound selected from the group consisting of: treatment fluids, additives, and any combination thereof; and the fluid for introduction into the subterranean formation is selected from among the plurality of candidate fluids.

A 3rd embodiment may include a method according to any one of the 1st and 2nd embodiments, the method further comprising injecting a first hydrocarbon fluid into the pore network of the first mini-reservoir device; and injecting a second hydrocarbon fluid into the pore network of the second mini-reservoir device.

A 4th embodiment may include a method according to the 3rd embodiment, wherein the first hydrocarbon fluid is injected before the first candidate fluid is injected; and further wherein the second hydrocarbon fluid is injected before the second candidate fluid is injected.

A 5th embodiment may include a method according to the 4th embodiment, wherein each of the first and second hydrocarbon fluids is injected in batch; wherein injection of the first hydrocarbon fluid is substantially complete before the first candidate fluid is injected; and wherein injection of the second hydrocarbon fluid is substantially complete before the second candidate fluid is injected.

A 6th embodiment may include a method according to any one of the 3rd-5th embodiments, wherein the first candidate fluid is injected at least partially concurrently with the first hydrocarbon fluid; and further wherein the second candidate fluid is injected at least partially concurrently with the second hydrocarbon fluid.

A 7th embodiment may include a method according to any one of the 3rd-6th embodiments, wherein each of the first and second hydrocarbon fluids is injected on a continuous flow basis.

An 8th embodiment may include a method according to any one of the foregoing embodiments, wherein each of the first candidate fluid and the second candidate fluid are injected at substantially the same time.

A 9th embodiment may include a method according to any one of the foregoing embodiments, wherein each of the first visual data and the second visual data are obtained while each of the first candidate fluid and the second candidate fluid is being injected into the mini-reservoir device at approximately equal drive pressure.

A 10th embodiment may include a method according to any one of the foregoing embodiments, wherein the pore network of the first mini-reservoir device comprises nano-pores; and further wherein the pore network of the second mini-reservoir device comprises nano-pores.

An 11th embodiment may include a method according to any one of the 3rd-7th embodiments, wherein each of the first and second hydrocarbon fluids have substantially similar compositions.

A 12th embodiment may include a method according to any one of the 3rd-7th and 11th embodiments, wherein each of the first and second hydrocarbon fluids have substantially similar compositions.

A 13th embodiment may include a method according to any one of the foregoing embodiments, wherein each candidate fluid comprises a surfactant.

A 14th embodiment may include a method according to any one of the foregoing embodiments, further comprising introducing the selected fluid into a subterranean formation in a fracturing fluid.

A 15th embodiment may include a method according to any one of the 13th and 14th embodiments, wherein selecting a fluid for introduction into the subterranean formation comprises selecting a candidate fluid that comprises a weakly emulsifying surfactant.

A 16th embodiment may include a method according to any one of the foregoing embodiments, wherein visual analysis of the first and second visual data comprises evaluating emulsion tendency.

A 17th embodiment may include a method according to the 16th embodiment, further comprising: agitating the first mini-reservoir device while the first mini-reservoir device contains one or more fluids in it; and agitating the second mini-reservoir device while the second mini-reservoir device contains one or more fluids in it.

An 18th embodiment may include a method comprising: injecting a hydrocarbon fluid into a pore network of a mini-reservoir device; injecting a second fluid into the pore network; determining saturation of the hydrocarbon fluid injected into the pore network; determining saturation of the second fluid injected into the pore network; and based at least in part upon determination of the saturation of each of the hydrocarbon fluid and the second fluid, determining an oil recovery factor associated with the second fluid.

A 19th embodiment may include a method according to the 18th embodiment, further comprising injecting a preliminary fluid into the pore network, and determining saturation of the preliminary fluid injected into the pore network; wherein determination of the oil recovery factor associated with the second fluid is further based at least in part upon the determination of the saturation of the preliminary fluid.

A 20th embodiment may include a method according to any one of the 18th and 19th embodiments, further comprising: injecting an additional portion of the hydrocarbon fluid into a pore network of a second mini-reservoir device; injecting a third fluid into the pore network of the second mini-reservoir device; determining saturation of the additional portion of the hydrocarbon fluid injected into the pore network of the second mini-reservoir device; determining saturation of the third fluid injected into the pore network of the second mini-reservoir device; and based at least in part upon determination of the saturation of each of the additional portion of the hydrocarbon fluid and the third fluid, determining a second oil recovery factor, said second oil recovery factor being associated with the third fluid.

A 21st embodiment may include a method according to the 20th embodiment, wherein each of the second fluid and the third fluid is a candidate treatment fluid from among a plurality of candidate treatment fluids.

A 22nd embodiment may include a method according to 21st embodiment, further comprising: based at least in part upon determination of the oil recovery factor and of the second oil recovery factor, selecting a treatment fluid, from among the plurality of candidate treatment fluids, for use in a subterranean formation.

A 23rd embodiment may include a method according to the 22nd embodiment, wherein the selected treatment fluid comprises a weakly emulsifying surfactant.

A 24th embodiment may include a method comprising: injecting a hydrocarbon fluid into each of a plurality of mini-reservoir devices, each mini-reservoir device comprising a pore network; injecting each of a plurality of candidate fluids into a respective one of the plurality of mini-reservoir devices; observing the relative characteristics of each of the plurality of candidate fluids in each respective mini-reservoir device; and based at least in part upon the observed relative characteristics, selecting a candidate fluid, from among the plurality of candidate fluids, for use in a subterranean formation.

A 25th embodiment may include a method according to the 24th embodiment, wherein each candidate fluid comprises a compound selected from the group consisting of: surfactants; corrosion inhibitors; scale inhibitors; gas injection gases; friction reducers; foaming agents; hydrate inhibitors; paraffin inhibitors; biocides; viscosifying agents; emulsion breakers; and combinations thereof.

A 26th embodiment may include a method comprising: injecting a first candidate fluid into a first pore network of a mini-reservoir device; injecting a second candidate fluid into a second pore network of the mini-reservoir device; obtaining first visual data of the flow of the first candidate fluid through the first pore network; obtaining second visual data of the flow of the second candidate fluid through the second pore network; and, based at least in part upon visual analysis of the first and second visual data, selecting a fluid for introduction into a subterranean formation.

A 27th embodiment may include a method according to the 26th embodiment, further comprising injecting a first hydrocarbon fluid into the first pore network; and injecting a second hydrocarbon fluid into the second pore network.

A 28th embodiment may include a method according to the 27th embodiment, wherein the first hydrocarbon fluid is injected before the first candidate fluid is injected; and further wherein the second hydrocarbon fluid is injected before the second candidate fluid is injected.

A 29th embodiment may include a method according to any one of the 27th and 28th embodiments, wherein each of the first and second hydrocarbon fluids are sourced from the same subterranean formation.

A 30th embodiment may include a method according to any one of the 26th-29th embodiments, wherein each candidate fluid comprises a surfactant.

A 31st embodiment may include a method according to the 30th embodiment, wherein the fluid for introduction into a subterranean formation is selected from a plurality of candidate fluids.

A 32nd embodiment may include a method according to any one of the 26th-31st embodiments, wherein the first candidate fluid and the second candidate fluid are injected at substantially the same time.

A 33rd embodiment may include a method according to any one of the 1st-17th embodiments, wherein each of the pore network of the first mini-reservoir device and the pore network of the second mini-reservoir device is configured to approximate a pore network within the subterranean formation.

A 34th embodiment may include a method according to any one of the 18th-23rd embodiments, wherein the pore network of the mini-reservoir device is configured to approximate a pore network within the subterranean formation.

A 35th embodiment may include a method according to any one of the 24th-25th embodiments, wherein each pore network of each mini-reservoir device is configured to approximate a pore network within the subterranean formation.

A 36th embodiment may include a method according to any one of the 26th-32nd embodiments, wherein each of the first and second pore networks is configured to approximate a pore network within the subterranean formation.

A 37th embodiment may include a method according to any one of the 1st, 3rd-17th, 24th-33rd, and 35th-36th embodiments, wherein each candidate fluid is from among a plurality of candidate fluids.

To facilitate a better understanding of the present disclosure, the following example according to some example embodiments is presented. In no way should such example be read to limit the scope of the invention to only the example provided below.

EXAMPLE

In this example, two different types of candidate surfactant were compared against each other and against a control fluid comprising no surfactant (here, 4% KCl solution). Relative oil recovery capabilities were analyzed based upon flow through a silica-based nanofluidic Porous Media Analog (PMA) device.

A. Set-Up

Crude oil obtained from the Eagle Ford shale formation (located in Texas) had an API number of 41.8. The oil composition analysis showed that it had a total acid number of 0.01 and a total base number of 1.97, suggesting that it contained more alkaline compounds, which are typically positively charged in nature. Two surfactants with significantly different chemistry were used during the experiments. One was a field standard non-emulsifying surfactant that usually does not generate emulsions with oil; the other was a weakly-emulsifying surfactant that usually generates a short-lived oil in water (water external) emulsion. Both surfactants were prepared in 4% KCl with a concentration of 2000 ppm, or approximately 2 gal/1,000 gal.

Figure 8:
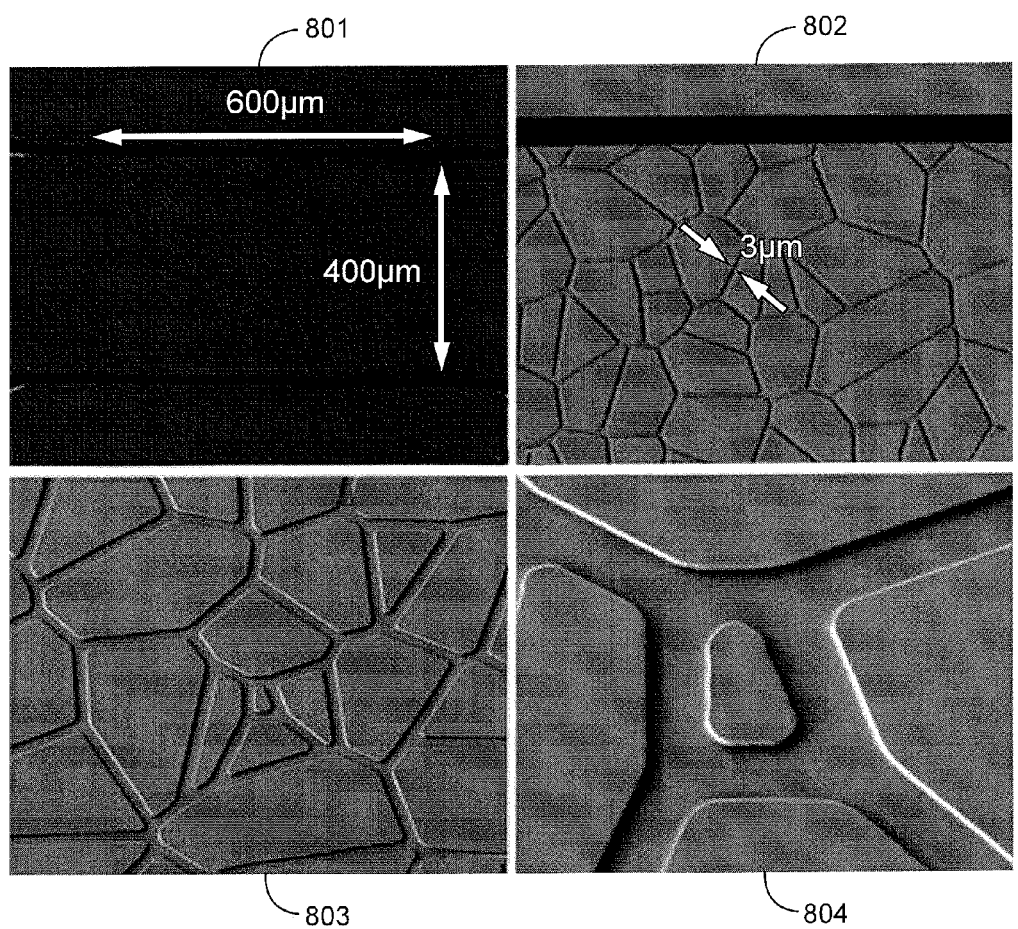
FIG. 8 is a set of images showing an example mini-reservoir device's pore network.

The nanofluidic PMA device was fabricated according to methods described by Mao and Han 2011. FIG. 8 is a series of 4 electron micrographs of the nanofluidic chip used in this Example. The porous network had an area of about 400×600 $\mu m^2$. Image 801 gives an overview of the device; image 802 shows a top view of the random porous network; image 803 shows a 30° tilted view of the random porous network; and image 804 shows a high magnification view of a portion of the pore structure.

The pore structures were defined in double-sided polished <100> silicon wafers (thickness=250 μm) with low-stress silicon nitride (~100 nm) on both sides. First, a random porous network consisting of nanochannels with an area of 400×600 $\mu m^2$ and channel width of 3 μm was defined using a deep reactive ion etching based on a Voronoi tessellation method described by Wu et al. 2012. The nano-channel depth was approximately 300 nm, which was defined as the pore throat size, and the estimated porosity was 20%. Next, two microchannels with widths of 10 μm were defined on both sides of the random porous network. Finally, a back side deep reactive ion etching through the wafer was performed to generate the inlet and outlet holes at the four ends of the microchannels. The fabricated device was then anodically bonded to a thin Pyrex coverslip (Pyrex 7740, 40×20× 0.25 mm) and treated with a silane chemical, resulting in oil-wet uniformity. To prevent contamination of the surface, the entire device was rinsed with deionized (DI) water and methanol, and then dried using nitrogen gas before use.

A set up similar to that described in FIG. 3 was used. A nitrogen source was connected to two capillary tubes through pressure regulators. The capillary tubes served as reservoirs of the various fluids used in this Example (oil, 4% KCl solution, 2000 ppm weakly-emulsifying surfactant solution, and 2000 ppm non-emulsifying surfactant solution). The capillary tubes were connected to the nano-fluidic device through tubing of inside diameter 150 μm and outside diameter 360 μm. Procedures were performed at ambient temperature. The device was cleaned between each use.

B. Methods

The crude oil was prefiltered using a 0.22 μm nylon filter, then injected at pressure of 10 psi to fill both microchannels and the nanochannels between the microchannels. The channel surface had a wettability that preferred oil to air. As a result, this process did not leave air trapped inside the nanofluidic device.

A constant flow of the crude oil through one of the two microchannels was established by maintaining a pressure difference of 10 psi between the inlet and the outlet of the microchannel (oil microchannel). The inlet pressure was regulated using a precision pressure regulator connected to a nitrogen gas cylinder, which was monitored by a digital pressure gauge. The outlet was open to the atmosphere. This flow established a pressure of 5 psig at the nanochannel-oil microchannel junction because the junction was located halfway between the inlet and outlet of the oil microchannel. This set-up and flow was repeated for each of three devices.

The KCl and each surfactant solution, separately, were injected into the other microchannel (water microchannel), at a pressure of 10 psig. The outlet of the water microchannel was also open to the atmosphere. After a constant flow of the surfactant solution was established, the pressure at the nanochannel water microchannel junction was also 5 psig because the junction was half-way between the inlet and outlet of the oil microchannel. Because the hydrodynamic resistance in the nanochannels was much higher than in the microchannels, most of the injected fluids moved through the microchannels. Thus, the contribution of flows in nanochannels to the flows in microchannels was negligible, and a stable pressure gradient and flow rate can be achieved in the microchannels.

While the flow of the crude oil into the oil microchannel was maintained at 10 psi, the inlet pressure of the water channel was progressively increased, which raised the pressure at the nanochannel water microchannel junction. For example, when the inlet pressure was raised to 20 psi, the pressure at the nanochannel water microchannel junction was raised to 10 psi, and the pressure difference across the microchannels from the water to oil sides was 5 psi. When the pressure difference exceeded the capillary pressure, the oil was drained from the nanochannels. The displacement pattern and efficiency were monitored and measured using an "OLYMPUS®" BX60 microscope (such as available from Olympus America Inc.) with 10× and 50× objectives.

C. Image Processing

To visualize the oil recovery and compare the oil displacement efficiency, image processing was conducted using "MATLAB®" software, available from MathWorks, Inc. During this process, image subtraction was used to highlight the contrast between the oil and water phase. Typically, a reference image (Image A, tiff format) was taken when the nanochannel was filled with oil. As the displacement progressed, another image (Image B, tiff format) was taken, and the change in the oil saturation can be detected with a direct subtraction of Image A from the new Image B.

D. Results

1. KCl Fluid Flooding

Figure 9:
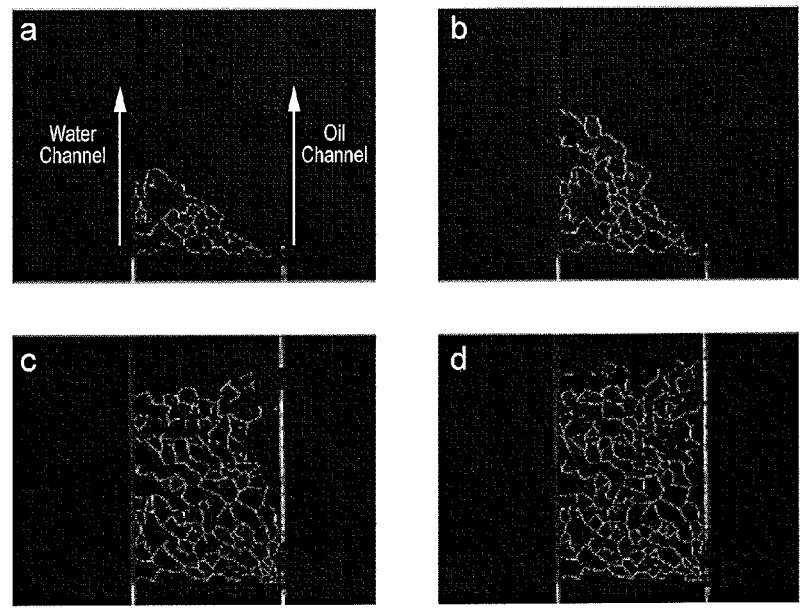
FIGS. 9a through 9d are processed images showing penetration of a candidate fluid into a mini-reservoir device's pore network, according to some embodiments of the present disclosure.

The non-surfactant-bearing fluid 4% KCl solution was injected into the nanofluidic device to displace the crude oil. FIG. 9 shows processed micrographs of crude oil displacement by the KCl at each of the following drive pressures (measured at inlet side): 38, 40, 45, and 50 psig, in each of FIGS. 9a, 9b, 9c, and 9d. Each drive pressure respectively corresponded to pressure difference of 11.5, 12.5, 15, and 17.5 psi across the random porous network. KCl breakthrough (that is, when the control fluid reached the oil channel) occurred at 38 psi. Importantly, it was observed that oil saturation did not decrease after breakthrough when the pressure was held constant. It was likely that most of the displacing fluid simply followed the path of the least resistance and left the majority of oil behind. Conversely, FIGS. 9a through 9d also indicated that oil saturation began to decrease with increasing pressure, suggesting sufficient pressure drop or drawdown could eventually overcome capillary forces and drive most of the oil out of the random porous network with a pore throat size of 300 nm.

2. Weakly-Emulsifying Surfactant Flooding

Figure 10:
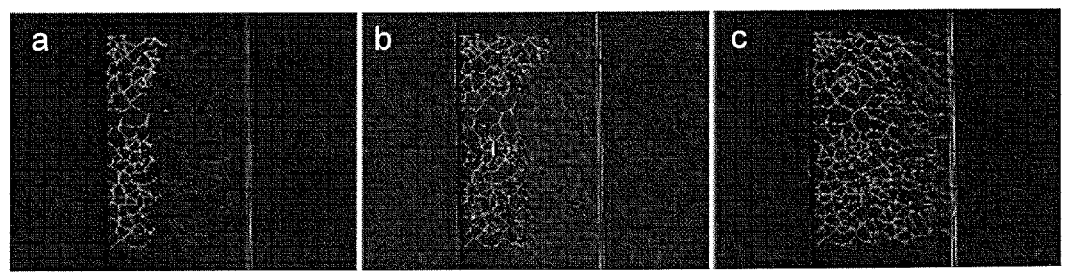
FIGS. 10a through 10c are processed images showing penetration of a candidate fluid into a mini-reservoir device's pore network, according to some embodiments of the present disclosure.
Figure 11:
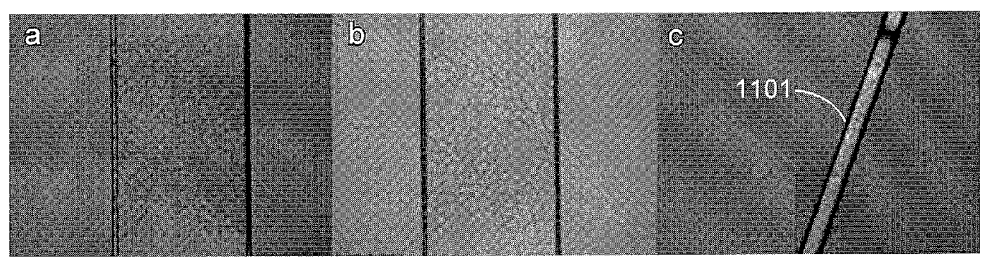
FIG. 11a is an optical micrograph of crude oil displacement using a candidate fluid according to some embodiments of the present disclosure.
FIG. 11b is an optical micrograph of crude oil displacement using a different candidate fluid according to some embodiments of the present disclosure.
FIG. 11c is an image of emulsified oil droplets recorded during an example carried out according to some embodiments of the present disclosure.

A weakly-emulsifying surfactant prepared in 4% KCl was injected into the nanofluidic device for crude oil displacement. FIG. 10 illustrates processed images of oil displacement at driving pressures (measured at inlet side) of: 20, 30, and 40 psi in each of FIGS. 10a, 10b, and 10c (corresponding to pressure differences of 5, 10, and 15 across the random porous network). As shown in FIGS. 11a and b, it was observed that the contrast between the crude oil and the surfactant solution was very low compared to the control fluid, and the breakthrough pattern was barely detected. FIG. 11a is an optical micrograph of crude oil displacement using the control fluid at 40 psig drive pressure; FIG. 11b shows crude oil displacement by weakly-emulsifying surfactant at 30 psig drive pressure. This effect may have been caused by the emulsified oil droplet or thin oil film attached onto the surface of the random porous network (see FIG. 11c), thereby lowering the contrast. The displacement pattern was more uniform when the oil was displaced using the WES rather than the control fluid, which indicated that the surfactant significantly lowered the capillary pressure and modified the front movement of the flooding fluid more so it was piston-like. Additionally, it was shown that, at 40 psi, more crude oil was recovered using the WES than the control fluid.

3. Non-Emulsifying Surfactant Flooding

Figure 12:
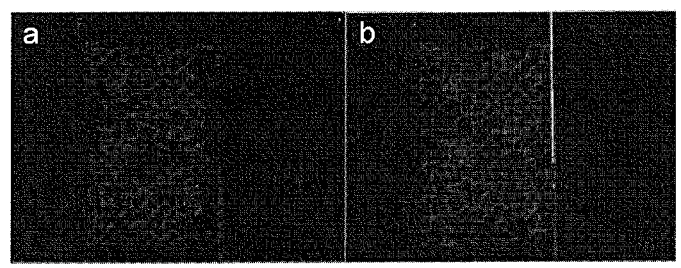
FIGS. 12a through 12b are processed images showing penetration of a candidate fluid into a mini-reservoir device's pore network, according to some embodiments of the present disclosure.

A non-emulsifying surfactant prepared in 4% KCl was injected into the nanofluidic device to displace the crude oil. FIGS. 12a and b illustrate the processed images of oil displacement at driving pressures of 20 and 30 psi (corresponding to the pressure difference of 5 and 10 psi across the random porous network). It appeared that breakthrough probably occurred at 30 psi; however, the oil saturation change between 20 and 30 psi was barely noticeable because of the ultra-low contrast.

The results of three tests on the nanofluidic device indicate that surfactants could significantly lower the capillary pressure, thus modifying the displacement front more so it was more piston-like. At the same driving pressure, compared to a non-surfactant-bearing control fluid, weakly-emulsifying surfactant yielded higher oil recovery. The piston-like displacement pattern of the weakly-emulsifying surfactant flooding could translate to higher oil recovery efficiency. Accordingly, the method provided a basis for selection of the weakly-emulsifying surfactant for use in the Eagle Ford formation from which the crude oil was taken.

E. Verification Study

Figure 13:
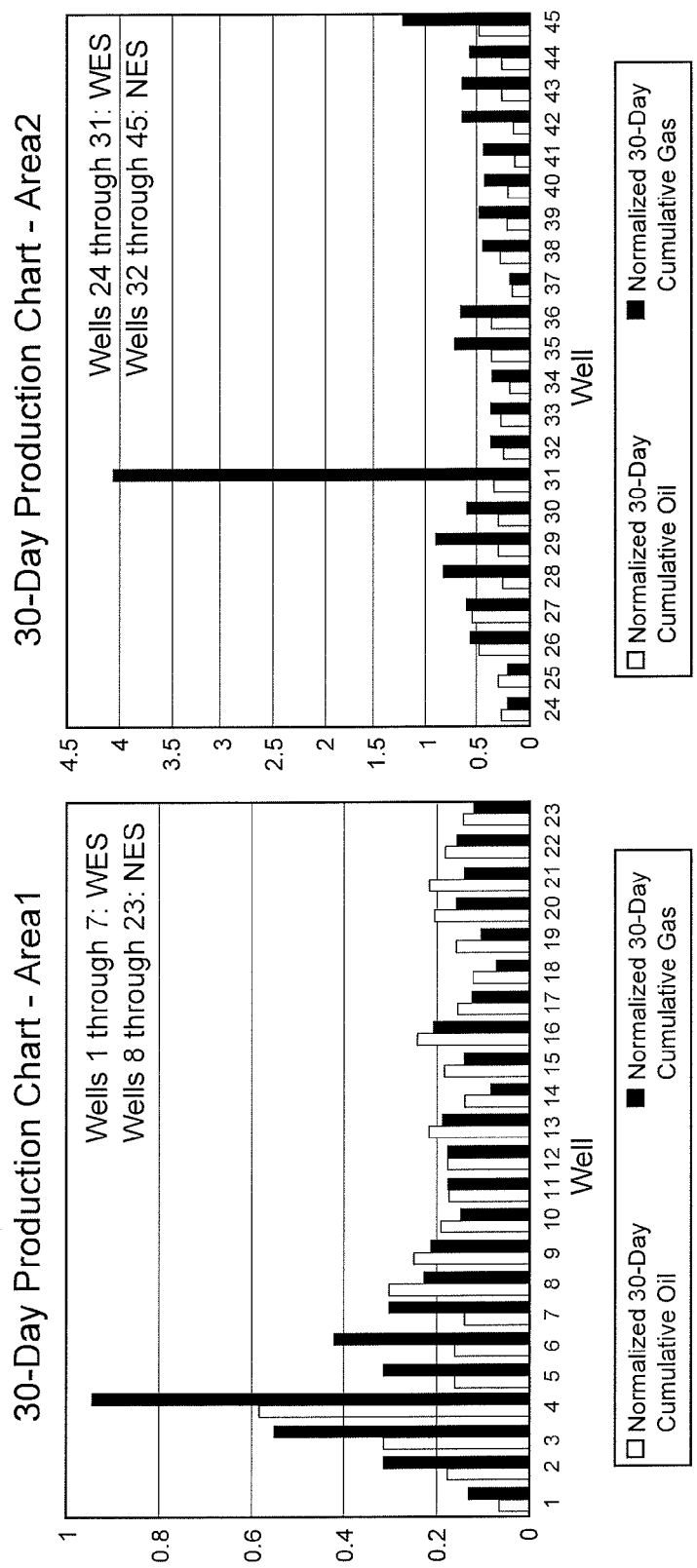
FIG. 13 is a set of production data graphs each showing production data from various wells according to certain embodiments of the present disclosure.
Figure 14:
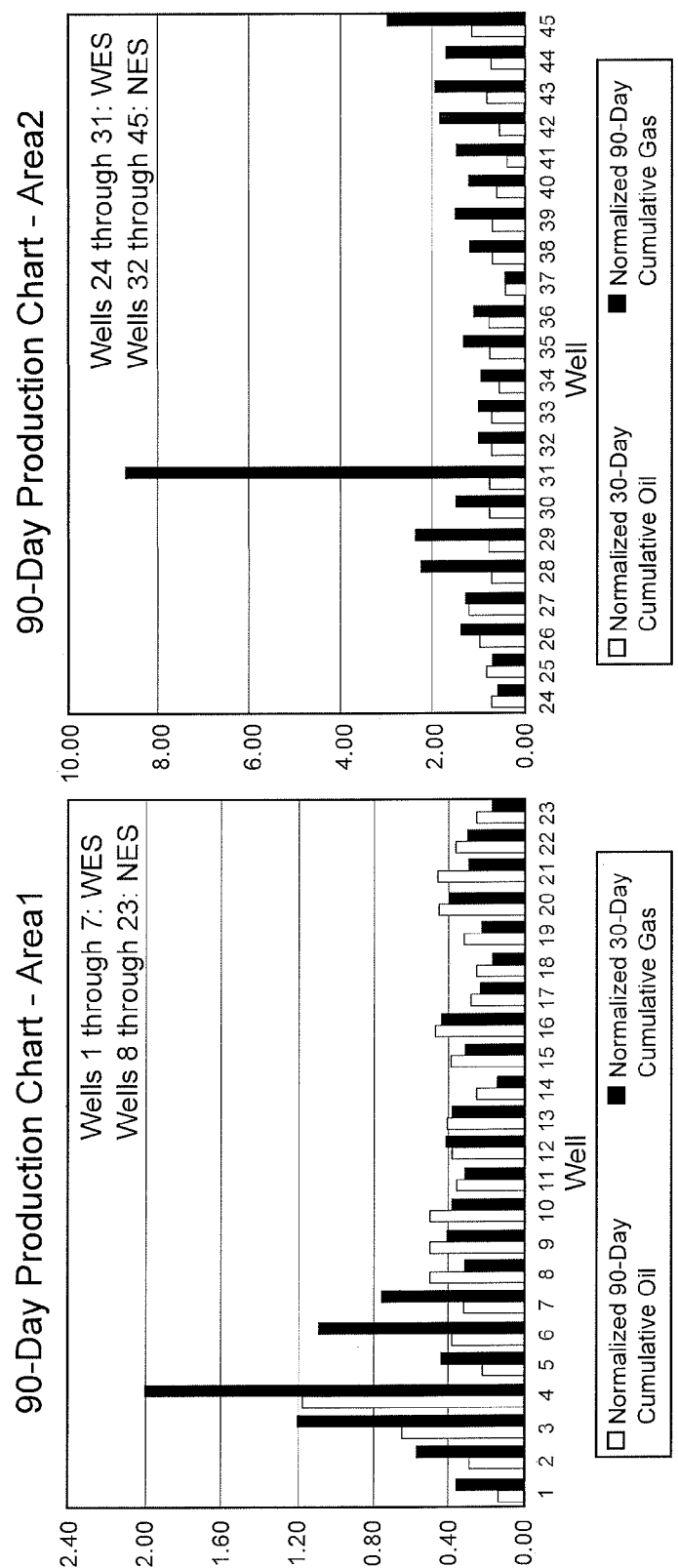
FIG. 14 is a set of production data graphs each showing production data from various wells according to certain embodiments of the present disclosure.
Figure 15:
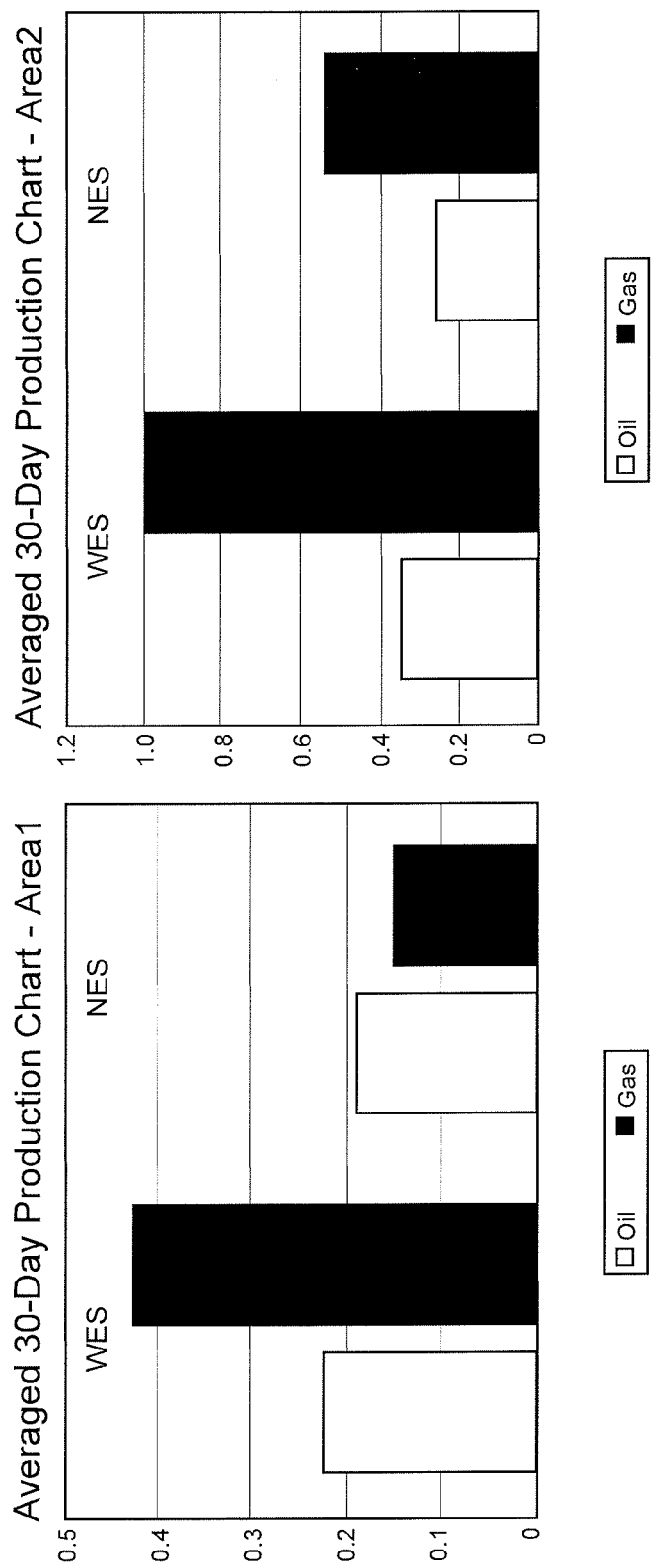
FIG. 15 is a set of production data graphs each showing production data from various wells according to certain embodiments of the present disclosure.
Figure 16:
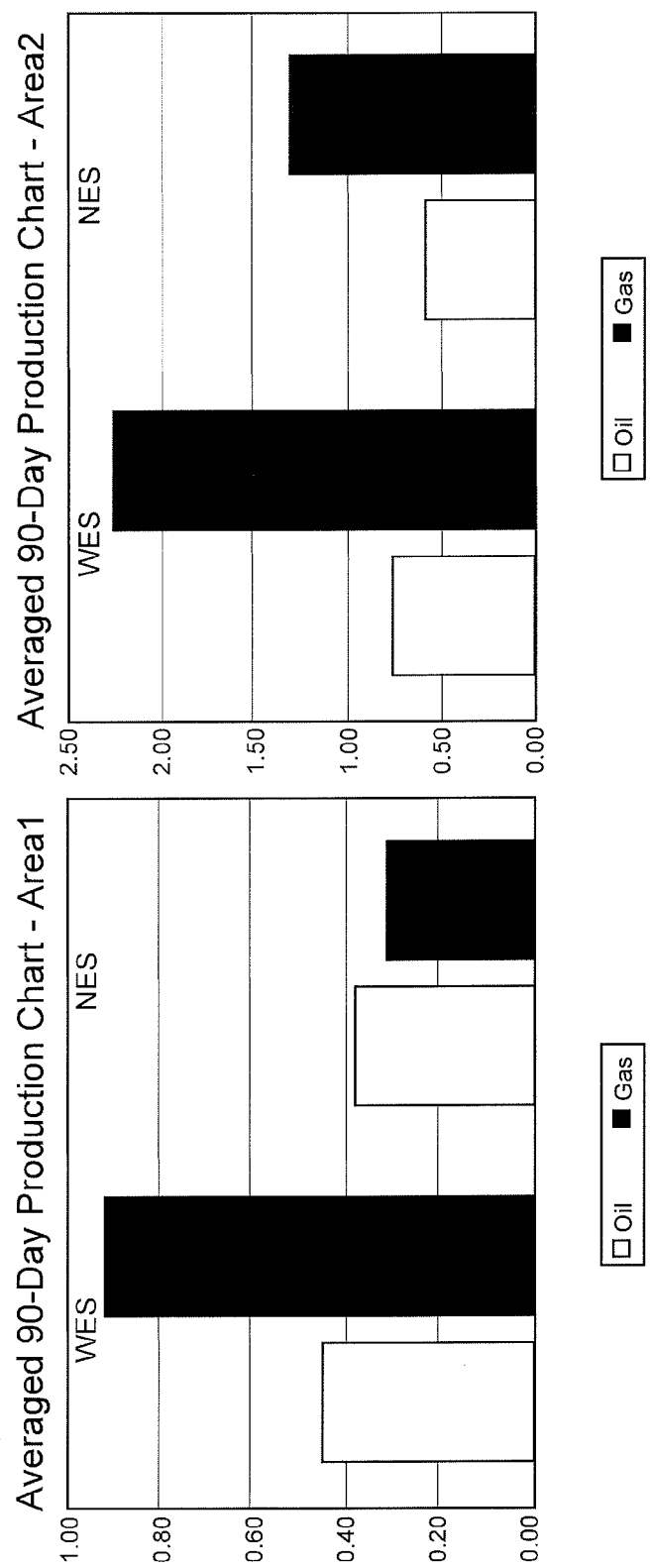
FIG. 16 is a set of production data graphs each showing production data from various wells according to certain embodiments of the present disclosure.

Production data of the weakly-emulsifying surfactant non-emulsifying surfactant in 45 wells separated in two areas in the Eagle Ford shale was compared to validate the laboratory results. Those wells were carefully chosen and believed to have minor difference in formation geometry and chemistry. The strategies of the fracturing process were also similar. Wells 1 through 7, in the first area, were treated with weakly-emulsifying surfactant. Wells 8 through 23 (also in the first area) were treated with non-emulsifying surfactant. Wells 24 through 31, in the second area, were treated with weakly-emulsifying surfactant; wells 32 through 45 (also in the second area) were treated with non-emulsifying surfactant. FIG. 13 shows production data for these wells in each of the two areas in the Eagle Ford for each surfactant up to 30 days. FIG. 14 similarly shows production data for these wells for each surfactant up to 90 days. The data shown in FIGS. 13 and 14 were normalized by lateral lengths and fracturing stages, which isolated the effect of production well size and surfactant usage. To compare the field performance, an average of the production data was calculated. As illustrated in FIGS. 15 and 16 (showing averaged production for each of the 30- and 90-day production data sets, respectively), the weakly-emulsifying surfactant yielded better performance in both sets of production data for the two different areas.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A method comprising:
   injecting a first candidate fluid into a pore network of a first mini-reservoir device, the pore network of the first mini-reservoir device being configured to approximate a pore network within a subterranean formation;
   injecting a second candidate fluid into a pore network of a second mini-reservoir device, the pore network of the second mini-reservoir device being configured to approximate a pore network within the subterranean formation;
   obtaining first visual data of the flow of the first candidate fluid through the first mini-reservoir device;
   obtaining second visual data of the flow of the second candidate fluid through the second mini-reservoir device; and
   based at least in part upon visual analysis of the first and second visual data, selecting a fluid for introduction into the subterranean formation.

2. The method of claim 1, wherein:
   the first and second candidate fluids are from among a plurality of candidate fluids;
   each one of the plurality of candidate fluids comprises a compound selected from the group consisting of: treatment fluids, additives, and any combination thereof; and
   the fluid for introduction into the subterranean formation is selected from among the plurality of candidate fluids.

3. The method of claim 1, further comprising:
   injecting a first hydrocarbon fluid into the pore network of the first mini-reservoir device; and
   injecting a second hydrocarbon fluid into the pore network of the second mini-reservoir device.

4. The method of claim 3, wherein the first candidate fluid is injected at least partially concurrently with the first hydrocarbon fluid; and further wherein the second candidate fluid is injected at least partially concurrently with the second hydrocarbon fluid.

5. The method of claim 4, wherein each of the first and second hydrocarbon fluids is injected on a continuous flow basis.

6. The method of claim 3, wherein each candidate fluid comprises a surfactant.

7. The method of claim 6, wherein selecting a fluid for introduction into the subterranean formation comprises selecting a candidate fluid that comprises a weakly emulsifying surfactant.

8. The method of claim 6, wherein visual analysis of the first and second visual data comprises evaluating emulsion tendency.

9. The method of claim 8, further comprising:
   agitating the first mini-reservoir device while the first mini-reservoir device contains one or more fluids in it; and
   agitating the second mini-reservoir device while the second mini-reservoir device contains one or more fluids in it.

10. The method of claim 1, wherein each of the first visual data and the second visual data are obtained while each of the first candidate fluid and the second candidate fluid is being injected into the mini-reservoir device at approximately equal drive pressure.

11. The method of claim 1, wherein the pore network of the first mini-reservoir device comprises nano-pores; and further wherein the pore network of the second mini-reservoir device comprises nano-pores.

12. A method comprising:
    injecting a hydrocarbon fluid into a pore network of a mini-reservoir device;
    injecting a second fluid into the pore network;
    determining saturation of the hydrocarbon fluid injected into the pore network;
    determining saturation of the second fluid injected into the pore network;
    based at least in part upon determination of the saturation of each of the hydrocarbon fluid and the second fluid, determining an oil recovery factor associated with the second fluid; and
    injecting a preliminary fluid into the pore network, and determining saturation of the preliminary fluid injected into the pore network; wherein determination of the oil recovery factor associated with the second fluid is further based at least in part upon the determination of the saturation of the preliminary fluid.

13. The method of claim 12, further comprising:
injecting an additional portion of the hydrocarbon fluid into a pore network of a second mini-reservoir device;
injecting a third fluid into the pore network of the second mini-reservoir device;
determining saturation of the additional portion of the hydrocarbon fluid injected into the pore network of the second mini-reservoir device;
determining saturation of the third fluid injected into the pore network of the second mini-reservoir device; and
based at least in part upon determination of the saturation of each of the additional portion of the hydrocarbon fluid and the third fluid, determining a second oil recovery factor, said second oil recovery factor being associated with the third fluid.

14. The method of claim 13, wherein each of the second fluid and the third fluid is a candidate treatment fluid from among a plurality of candidate treatment fluids.

15. The method of claim 14, further comprising:
based at least in part upon determination of the oil recovery factor and of the second oil recovery factor, selecting a treatment fluid, from among the plurality of candidate treatment fluids, that comprises a weakly emulsifying surfactant for use in a subterranean formation.

16. A method comprising:
injecting a first candidate fluid into a first pore network of a mini-reservoir device;
injecting a second candidate fluid into a second pore network of the mini-reservoir device;
obtaining first visual data of the flow of the first candidate fluid through the first pore network;
obtaining second visual data of the flow of the second candidate fluid through the second pore network;
injecting a first hydrocarbon fluid into the first pore network;
injecting a second hydrocarbon fluid into the second pore network; and
based at least in part upon visual analysis of the first and second visual data, selecting a fluid for introduction into a subterranean formation.

17. The method of claim 16, wherein the first hydrocarbon fluid is injected before the first candidate fluid is injected; and further wherein the second hydrocarbon fluid is injected before the second candidate fluid is injected.

18. The method of claim 17, wherein each of the first and second hydrocarbon fluids are sourced from the same subterranean formation.

19. The method of claim 18, wherein each candidate fluid comprises a surfactant; and further wherein the fluid for introduction into a subterranean formation is selected from a plurality of candidate fluids.

* * * * *